(12) United States Patent
Sinnott et al.

(10) Patent No.: US 8,951,263 B2
(45) Date of Patent: *Feb. 10, 2015

(54) ORTHOPEDIC SUTURE PASSER AND METHOD

(71) Applicant: Smith & Nephew, Inc., Memphis, TN (US)

(72) Inventors: M. Mary Sinnott, Logan, UT (US); Kwan-Ho Chan, Singapore (SG); Patrick M. White, West Chester, PA (US); T. Wade Fallin, Hyde Park, UT (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/865,737

(22) Filed: Apr. 18, 2013

(65) Prior Publication Data

US 2013/0231669 A1 Sep. 5, 2013

Related U.S. Application Data

(63) Continuation-in-part of application No. 13/527,648, filed on Jun. 20, 2012, and a continuation-in-part of application No. 13/527,765, filed on Jun. 20, 2012.

(60) Provisional application No. 61/568,137, filed on Dec. 7, 2011, provisional application No. 61/505,992, filed on Jul. 8, 2011, provisional application No. 61/506,000, filed on Jul. 8, 2011, provisional application No. 61/506,004, filed on Jul. 8, 2011.

(51) Int. Cl.
*A61B 17/58* (2006.01)
*A61B 17/60* (2006.01)
*A61F 2/00* (2006.01)
*A61B 17/17* (2006.01)
*A61B 17/88* (2006.01)
*A61B 17/062* (2006.01)
*A61B 17/04* (2006.01)

(52) U.S. Cl.
CPC ............ *A61B 17/1796* (2013.01); *A61B 17/88* (2013.01); *A61B 17/1714* (2013.01); *A61B 17/1739* (2013.01); *A61B 17/0625* (2013.01); *A61B 2017/1775* (2013.01); *A61B 17/0483* (2013.01)
USPC ............................ 606/96; 606/103; 606/104

(58) Field of Classification Search
USPC ............................................. 606/88, 89, 103
See application file for complete search history.

(56) References Cited

U.S. PATENT DOCUMENTS 919,138 A 4/1909 Drake et al.
1,037,864 A 9/1912 Carlson et al.

(Continued)

FOREIGN PATENT DOCUMENTS

WO WO03/007799 A2 1/2003
WO WO2004/002324 A1 1/2004

OTHER PUBLICATIONS

2008 Arthrex Inc., "The Arthrex Scorpion" 6 pages.

(Continued)

*Primary Examiner* — Andrew Yang
(74) *Attorney, Agent, or Firm* — David A. Chambers

(57) ABSTRACT

Instruments and techniques to pass a suture are presented. In one illustrative example, a suture passer includes a guide operable to guide the formation of a tunnel in a bone and guide passage of a suture through the tunnel so formed.

21 Claims, 32 Drawing Sheets

(56) References Cited

U.S. PATENT DOCUMENTS

| | | |
|---|---|---|
| 1,449,087 A | 3/1923 | Bugbee |
| 1,635,066 A | 7/1927 | Wells |
| 1,815,725 A | 7/1931 | Pilling et al. |
| 1,822,330 A | 9/1931 | Ainslie |
| 1,856,721 A | 5/1932 | Nagelmann |
| 1,918,700 A | 7/1933 | Harris |
| 1,933,024 A | 10/1933 | Nagelmann |
| 1,981,651 A | 11/1934 | Logan |
| 2,240,330 A | 4/1941 | Flagg et al. |
| 2,269,963 A | 1/1942 | Wappler |
| 2,286,578 A | 6/1942 | Sauter |
| 2,291,413 A * | 7/1942 | Siebrandt ............... 606/103 |
| 2,301,500 A | 11/1942 | Anderson |
| 2,577,240 A | 12/1951 | Findley |
| 2,697,433 A | 12/1954 | Zehnder |
| 2,738,790 A | 3/1956 | Todt, Sr. et al. |
| 3,013,559 A | 12/1961 | Thomas |
| 3,090,386 A | 5/1963 | Curtis |
| 3,470,875 A | 10/1969 | Johnson |
| 3,638,653 A | 2/1972 | Berry |
| 3,840,017 A | 10/1974 | Violante |
| 3,842,840 A | 10/1974 | Schweizer |
| 3,946,740 A | 3/1976 | Bassett |
| 4,109,658 A | 8/1978 | Hughes |
| 4,164,225 A | 8/1979 | Johnson et al. |
| 4,172,458 A | 10/1979 | Pereyra |
| 4,224,947 A | 9/1980 | Fukuda |
| 4,345,601 A | 8/1982 | Fukuda |
| 4,373,530 A | 2/1983 | Kilejian |
| 4,406,237 A | 9/1983 | Eguchi et al. |
| 4,417,532 A | 11/1983 | Yasukata |
| 4,493,323 A | 1/1985 | Albright et al. |
| 4,596,249 A | 6/1986 | Freda et al. |
| 4,686,972 A | 8/1987 | Kurland |
| 4,739,751 A | 4/1988 | Sapega et al. |
| 4,781,182 A | 11/1988 | Purnell et al. |
| 4,823,780 A | 4/1989 | Odensten et al. |
| 4,836,205 A | 6/1989 | Barrett |
| 4,883,048 A | 11/1989 | Purnell et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 4,964,861 A | 10/1990 | Agee et al. |
| 5,059,201 A | 10/1991 | Asnis |
| 5,112,335 A | 5/1992 | Laboureau et al. |
| 5,112,337 A | 5/1992 | Paulos et al. |
| 5,217,471 A | 6/1993 | Burkhart |
| 5,222,977 A | 6/1993 | Esser |
| 5,281,237 A | 1/1994 | Gimpelson |
| 5,312,422 A | 5/1994 | Trott |
| 5,318,577 A | 6/1994 | Li |
| 5,336,229 A | 8/1994 | Noda |
| 5,397,325 A | 3/1995 | Della Badia et al. |
| 5,431,666 A | 7/1995 | Sauer et al. |
| 5,433,722 A | 7/1995 | Sharpe et al. |
| 5,439,467 A | 8/1995 | Benderev et al. |
| 5,454,823 A | 10/1995 | Richardson et al. |
| 5,462,562 A | 10/1995 | Elkus |
| 5,474,565 A | 12/1995 | Trott |
| 5,499,991 A | 3/1996 | Garman et al. |
| 5,520,693 A | 5/1996 | McGuire et al. |
| 5,522,820 A | 6/1996 | Caspari et al. |
| 5,544,664 A | 8/1996 | Benderev et al. |
| 5,562,686 A | 10/1996 | Sauer et al. |
| 5,571,119 A | 11/1996 | Atala |
| 5,573,542 A | 11/1996 | Stevens |
| 5,575,801 A | 11/1996 | Habermeyer et al. |
| 5,618,290 A | 4/1997 | Toy et al. |
| 5,632,752 A | 5/1997 | Buelna |
| 5,645,552 A | 7/1997 | Sherts |
| 5,662,663 A | 9/1997 | Shallman |
| 5,662,664 A | 9/1997 | Gordon et al. |
| 5,665,096 A | 9/1997 | Yoon |
| 5,690,653 A | 11/1997 | Richardson et al. |
| 5,713,908 A | 2/1998 | Jameel et al. |
| 5,713,910 A | 2/1998 | Gordon et al. |
| 5,730,747 A | 3/1998 | Ek et al. |
| 5,741,277 A | 4/1998 | Gordon et al. |
| 5,741,278 A | 4/1998 | Stevens |
| 5,741,279 A | 4/1998 | Gordon et al. |
| 5,741,281 A | 4/1998 | Martin |
| 5,766,186 A | 6/1998 | Faraz et al. |
| 5,776,150 A | 7/1998 | Nolan et al. |
| 5,792,153 A | 8/1998 | Swain et al. |
| 5,797,927 A | 8/1998 | Yoon |
| 5,860,992 A | 1/1999 | Daniel et al. |
| 5,871,488 A | 2/1999 | Tovey et al. |
| 5,902,311 A | 5/1999 | Andreas et al. |
| 5,904,692 A | 5/1999 | Steckel et al. |
| 5,908,426 A | 6/1999 | Pierce |
| 5,919,199 A | 7/1999 | Mers Kelly et al. |
| 5,921,994 A | 7/1999 | Andreas et al. |
| 5,928,252 A | 7/1999 | Steadman et al. |
| 5,947,982 A | 9/1999 | Duran |
| 5,968,050 A | 10/1999 | Torrie |
| 5,980,538 A | 11/1999 | Fuchs et al. |
| 5,984,933 A | 11/1999 | Yoon |
| 6,022,360 A | 2/2000 | Reimels et al. |
| 6,036,699 A | 3/2000 | Andreas et al. |
| 6,051,006 A | 4/2000 | Shluzas et al. |
| 6,071,289 A | 6/2000 | Stefanchik et al. |
| 6,074,403 A | 6/2000 | Nord |
| 6,096,051 A | 8/2000 | Kortenbach et al. |
| 6,136,010 A | 10/2000 | Modesitt et al. |
| 6,143,004 A | 11/2000 | Davis et al. |
| 6,156,039 A | 12/2000 | Thal |
| 6,187,011 B1 | 2/2001 | Torrie |
| 6,197,035 B1 | 3/2001 | Loubens et al. |
| 6,217,592 B1 | 4/2001 | Freda et al. |
| 6,270,503 B1 | 8/2001 | Schmieding |
| 6,296,659 B1 | 10/2001 | Foerster |
| 6,332,889 B1 | 12/2001 | Sancoff et al. |
| 6,475,135 B1 | 11/2002 | Levy |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,582,453 B1 | 6/2003 | Tran et al. |
| 6,585,730 B1 | 7/2003 | Foerster |
| 6,605,096 B1 | 8/2003 | Ritchart |
| 6,723,107 B1 | 4/2004 | Skiba et al. |
| 6,725,082 B2 | 4/2004 | Sati et al. |
| 6,770,076 B2 | 8/2004 | Foerster |
| 6,770,084 B1 | 8/2004 | Bain et al. |
| 6,802,807 B2 | 10/2004 | Anderson et al. |
| 6,855,157 B2 | 2/2005 | Foerster et al. |
| 6,878,150 B1 | 4/2005 | McGuire et al. |
| 6,893,448 B2 | 5/2005 | O'Quinn et al. |
| 6,896,686 B2 | 5/2005 | Weber |
| 6,911,034 B2 | 6/2005 | Nobles et al. |
| 6,936,054 B2 | 8/2005 | Chu |
| 6,984,237 B2 | 1/2006 | Hatch et al. |
| 6,997,932 B2 | 2/2006 | Dreyfuss et al. |
| 7,025,770 B2 | 4/2006 | McGuire et al. |
| 7,083,638 B2 | 8/2006 | Foerster |
| 7,090,686 B2 | 8/2006 | Nobles et al. |
| 7,112,208 B2 | 9/2006 | Morris et al. |
| 7,118,583 B2 | 10/2006 | O'Quinn et al. |
| 7,198,631 B2 | 4/2007 | Kanner et al. |
| 7,232,448 B2 | 6/2007 | Battles et al. |
| 7,285,124 B2 | 10/2007 | Foerster |
| 7,297,145 B2 | 11/2007 | Woloszko et al. |
| 7,329,264 B2 | 2/2008 | Merves |
| 7,377,926 B2 | 5/2008 | Topper et al. |
| 7,449,024 B2 | 11/2008 | Stafford |
| 7,544,199 B2 | 6/2009 | Bain et al. |
| 7,572,265 B2 | 8/2009 | Stone et al. |
| 7,575,578 B2 | 8/2009 | Wetzler et al. |
| 7,585,305 B2 | 9/2009 | Dreyfuss |
| 7,608,084 B2 | 10/2009 | Oren et al. |
| 7,695,494 B2 | 4/2010 | Foerster |
| 7,717,912 B2 | 5/2010 | Woloszko et al. |
| 7,722,630 B1 | 5/2010 | Stone et al. |

(56) References Cited

U.S. PATENT DOCUMENTS

| | | | |
|---|---|---|---|
| 7,727,256 | B2 | 6/2010 | McGregor |
| 7,758,597 | B1 | 7/2010 | Tran et al. |
| 7,771,438 | B2 | 8/2010 | Dreyfuss et al. |
| 7,815,654 | B2 | 10/2010 | Chu |
| 7,879,046 | B2 | 2/2011 | Weinert et al. |
| 7,879,048 | B2 | 2/2011 | Bain et al. |
| 7,883,519 | B2 | 2/2011 | Oren et al. |
| 7,922,744 | B2 | 4/2011 | Morris et al. |
| 7,963,972 | B2 | 6/2011 | Foerster et al. |
| 7,972,344 | B2 | 7/2011 | Murray et al. |
| 8,110,000 | B2 | 2/2012 | Collins |
| 8,147,505 | B2 | 4/2012 | Delli-Santi |
| 8,409,225 | B2 | 4/2013 | Bull |
| 8,449,552 | B2 | 5/2013 | Sanders |
| 8,551,123 | B2 | 10/2013 | Pandya |
| 2001/0037119 | A1 | 11/2001 | Schmieding |
| 2002/0147456 | A1 | 10/2002 | Diduch et al. |
| 2002/0173800 | A1 | 11/2002 | Dreyfuss et al. |
| 2003/0078599 | A1 | 4/2003 | O'Quinn et al. |
| 2003/0195528 | A1 | 10/2003 | Ritchart |
| 2003/0220659 | A1 | 11/2003 | Schmieding et al. |
| 2003/0233106 | A1 | 12/2003 | Dreyfuss |
| 2004/0010273 | A1 | 1/2004 | Diduch et al. |
| 2004/0015177 | A1 | 1/2004 | Chu |
| 2004/0138682 | A1 | 7/2004 | Onuki et al. |
| 2004/0249394 | A1 | 12/2004 | Morris et al. |
| 2005/0165419 | A1 | 7/2005 | Sauer et al. |
| 2005/0240226 | A1 | 10/2005 | Foerster et al. |
| 2006/0052801 | A1 | 3/2006 | Dreyfuss et al. |
| 2006/0241658 | A1 | 10/2006 | Cerundolo |
| 2006/0271060 | A1 | 11/2006 | Gordon |
| 2007/0060953 | A1 | 3/2007 | Morris et al. |
| 2007/0118150 | A1 | 5/2007 | Weber |
| 2007/0149986 | A1 | 6/2007 | Morris et al. |
| 2007/0179524 | A1 | 8/2007 | Weber et al. |
| 2007/0233128 | A1 | 10/2007 | Schmieding et al. |
| 2008/0015594 | A1 | 1/2008 | Ritchart et al. |
| 2008/0097482 | A1 | 4/2008 | Bain et al. |
| 2009/0036905 | A1 | 2/2009 | Schmieding |
| 2009/0062816 | A1 | 3/2009 | Weber |
| 2009/0062819 | A1 | 3/2009 | Burkhart et al. |
| 2009/0131956 | A1 | 5/2009 | Dewey et al. |
| 2009/0222040 | A1 | 9/2009 | Foerster |
| 2009/0222041 | A1 | 9/2009 | Foerster |
| 2009/0318965 | A1 | 12/2009 | Burkhart |
| 2010/0137889 | A1 | 6/2010 | Oren et al. |
| 2010/0152752 | A1 | 6/2010 | Denove et al. |
| 2010/0191283 | A1 | 7/2010 | Foerster et al. |
| 2010/0249806 | A1 | 9/2010 | Oren et al. |
| 2010/0268256 | A1 | 10/2010 | Dreyfuss et al. |
| 2011/0009867 | A1 | 1/2011 | Oren |
| 2011/0066165 | A1 | 3/2011 | Skinlo et al. |
| 2011/0144647 | A1 | 6/2011 | Appenzeller et al. |
| 2011/0208198 | A1 | 8/2011 | Anderson et al. |

OTHER PUBLICATIONS

Blitz, et al. Plantar Plate Repair of the Second Metatarsophalangeal Joint: Technique and Tips. Journal of Foot & Ankle Surgery, 2004 43(4):266-270.

Coughlin, et al. Second MTP Joint Instability: Grading of the Deformity and Description of Surgical Repair of Capsular Insufficiency. The Physician and Sportmedicine, Sep. 3, 2011, 39(3):132-141.

Fleming and Camasta, Plantar Plate Dysfunction. Chapter 4, (2002) pp. 22-28, http://www.podiatryinstitute.com/pdfs/Update_2002/20029_04.pdf.

Gregg et al., "Plantar Plate Repair and Weil Osteotomy for Metatarsophalangeal Joint Instability" Foot and Ankle Surgery, (2007) 13:116-121.

Nery et al., "Lesser Metatarsophalangeal Joint Instability: Prospective Evaluation and Repair of Plantar Plate and Capsular Insufficiency" Foot and Ankle International, Apr. 2012 vol. 33(4) pp. 301-311.

Weil, et al. "Anatomic Plantar Plate Repair Using the Weil Metatarsal Osteotomy Approach" Foot and Ankle Specialist, Jun. 22, 2011 vol. 4 pp. 145-150. Originally published online on Mar. 18, 2011 http://fas.sagepub.com/content/4/3/145.

* cited by examiner

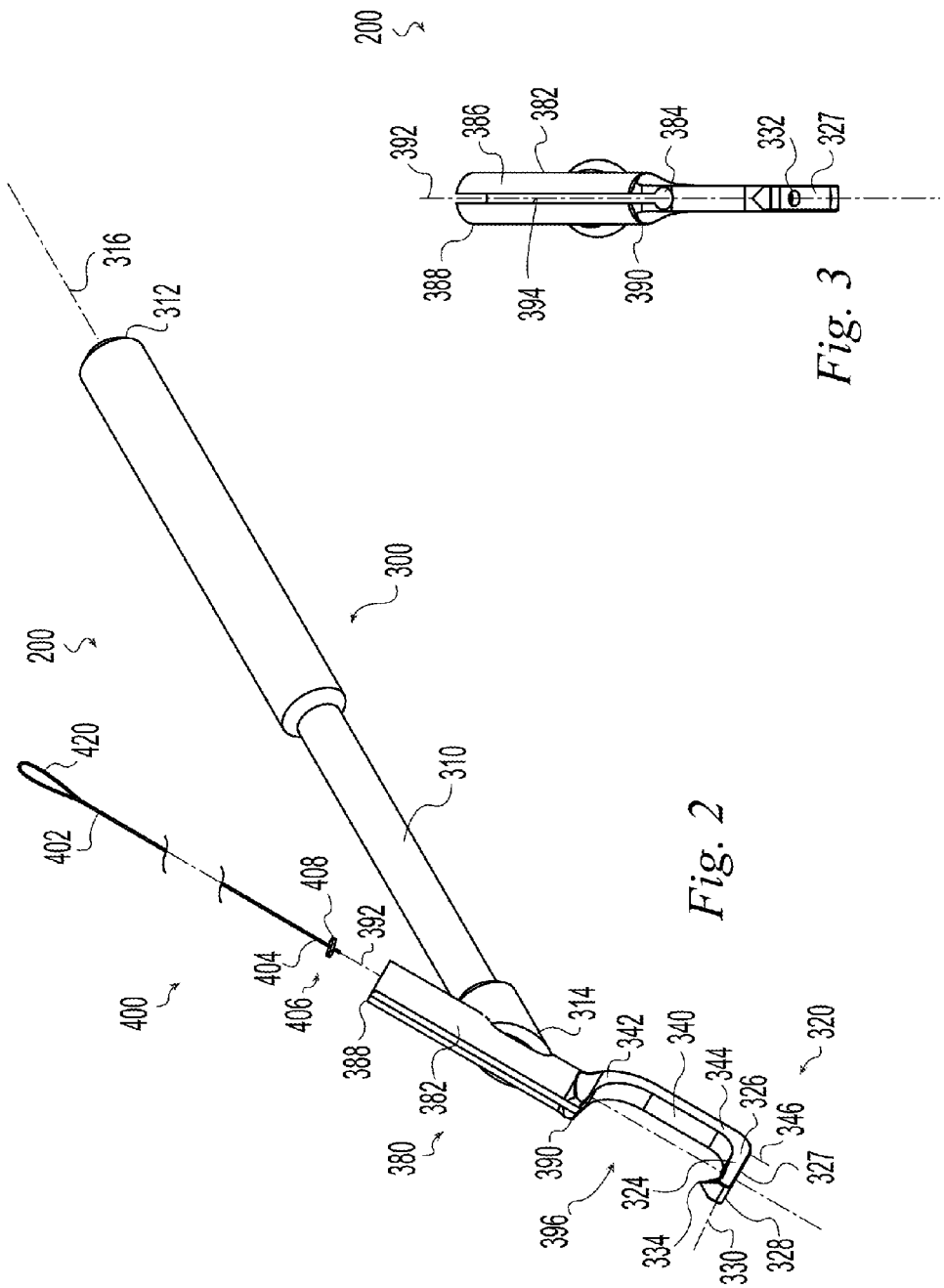

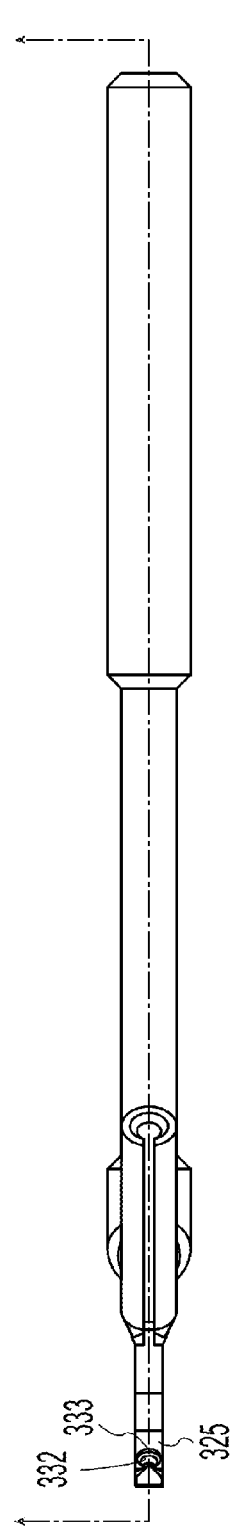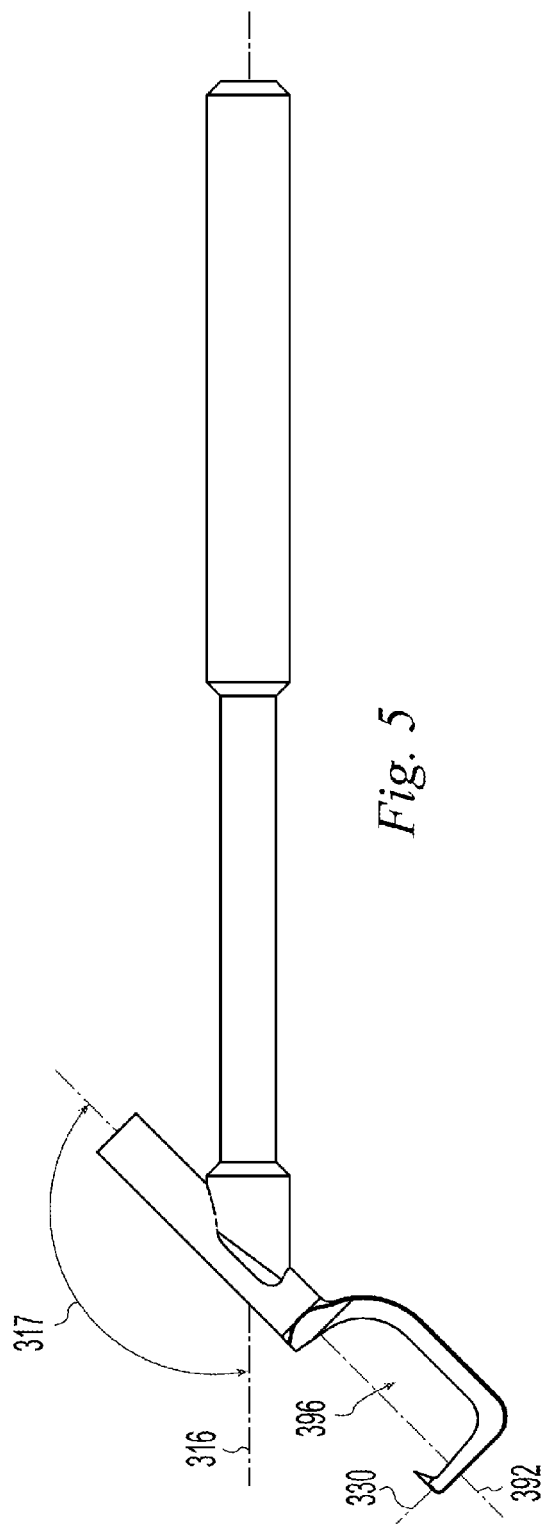

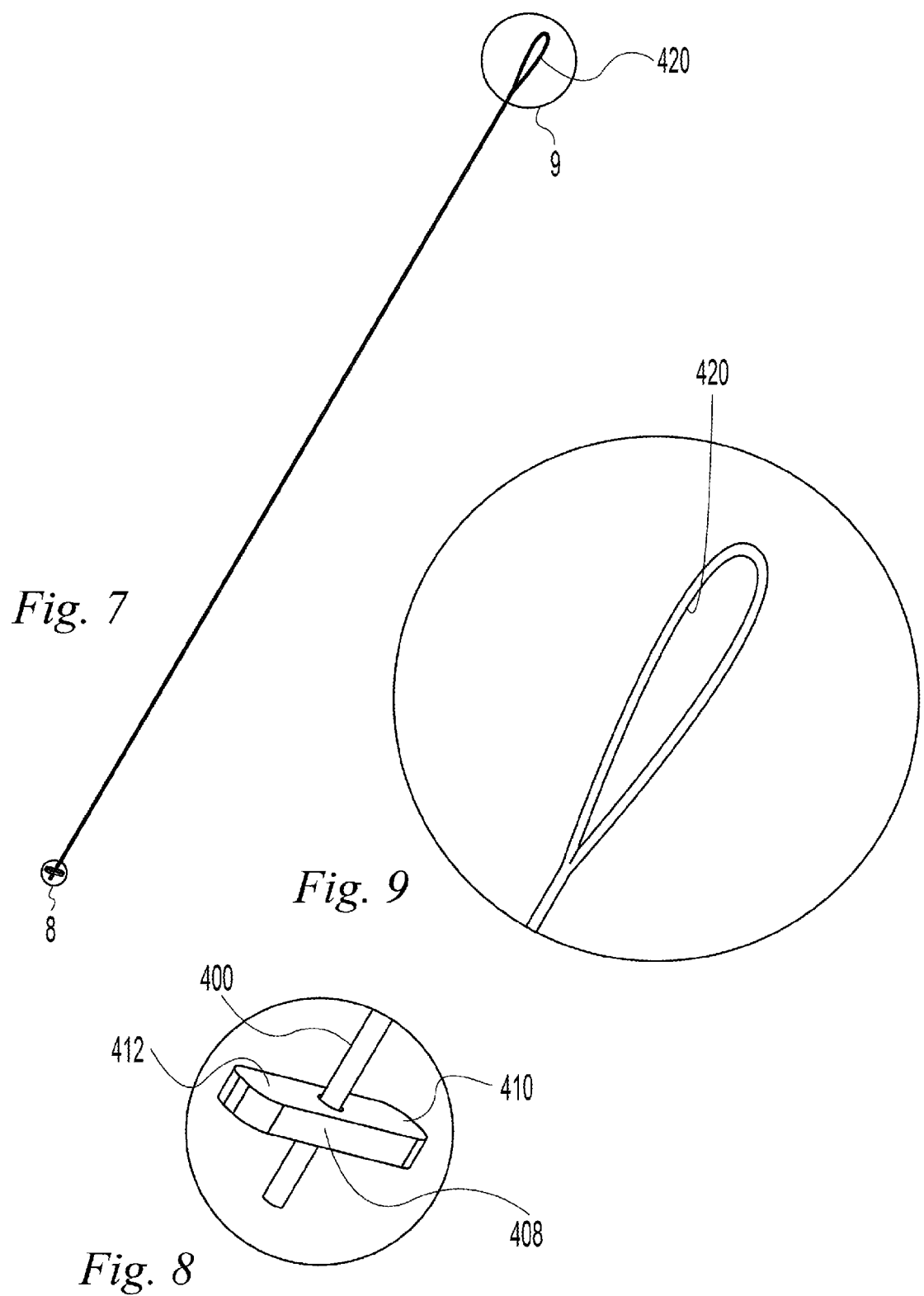

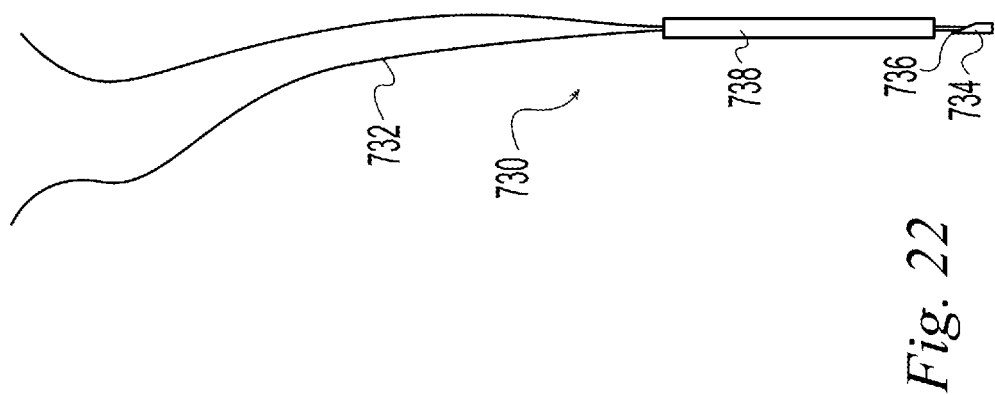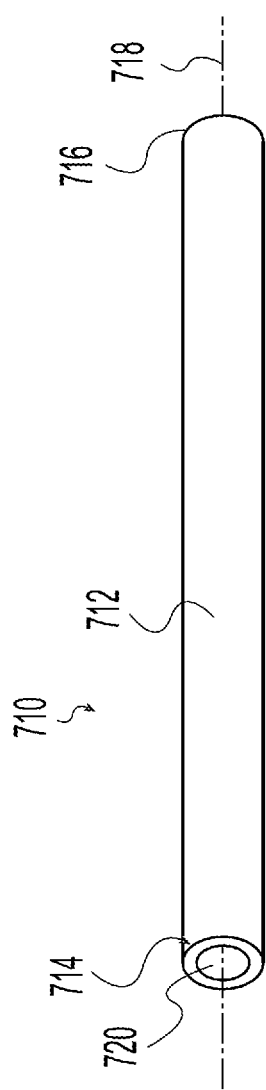

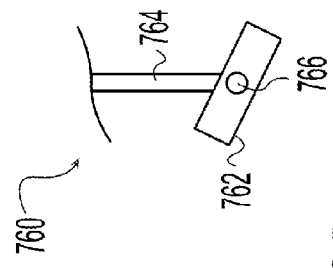
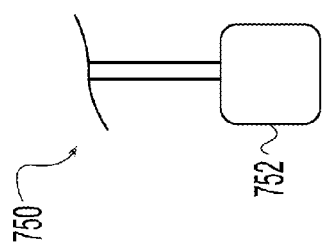
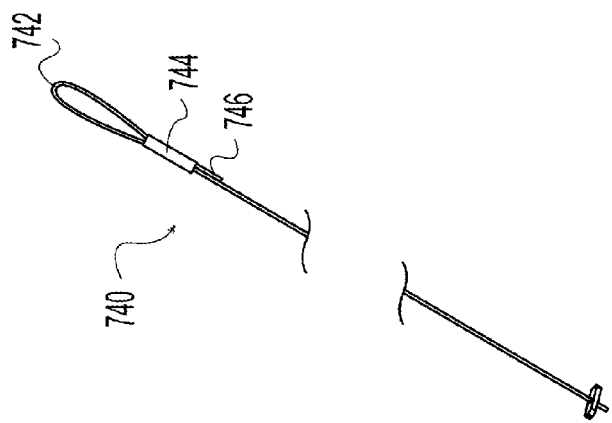

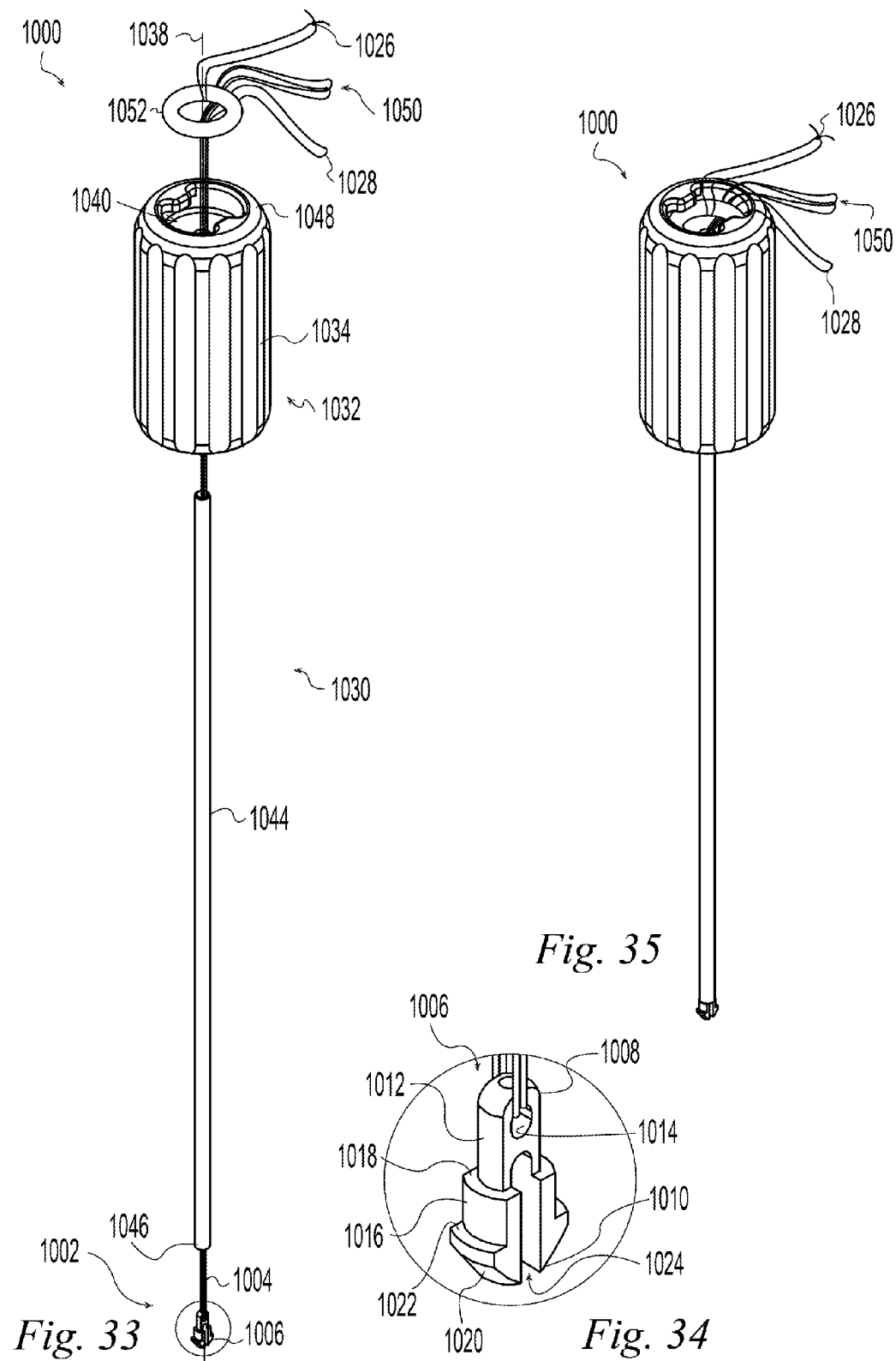

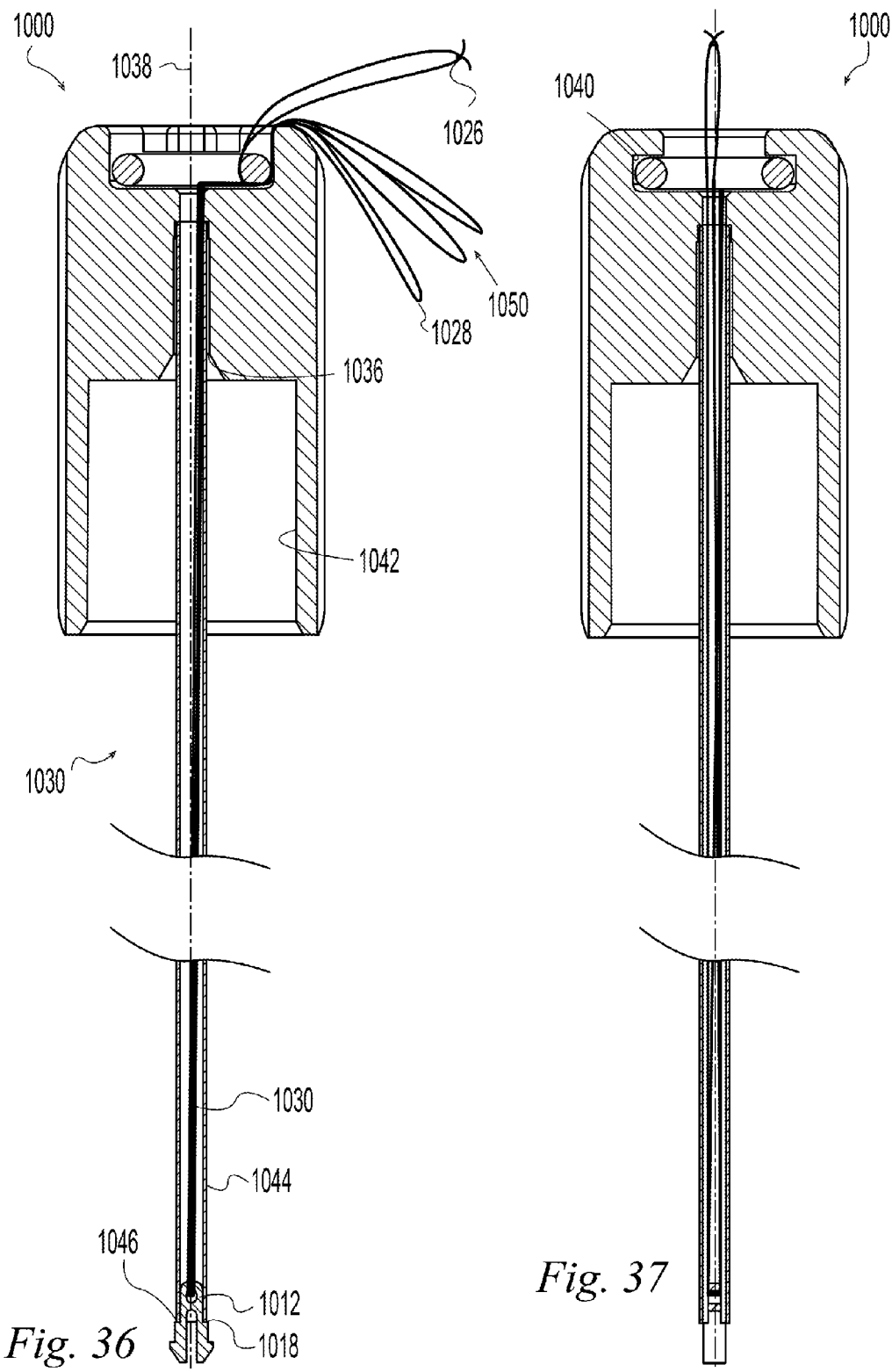

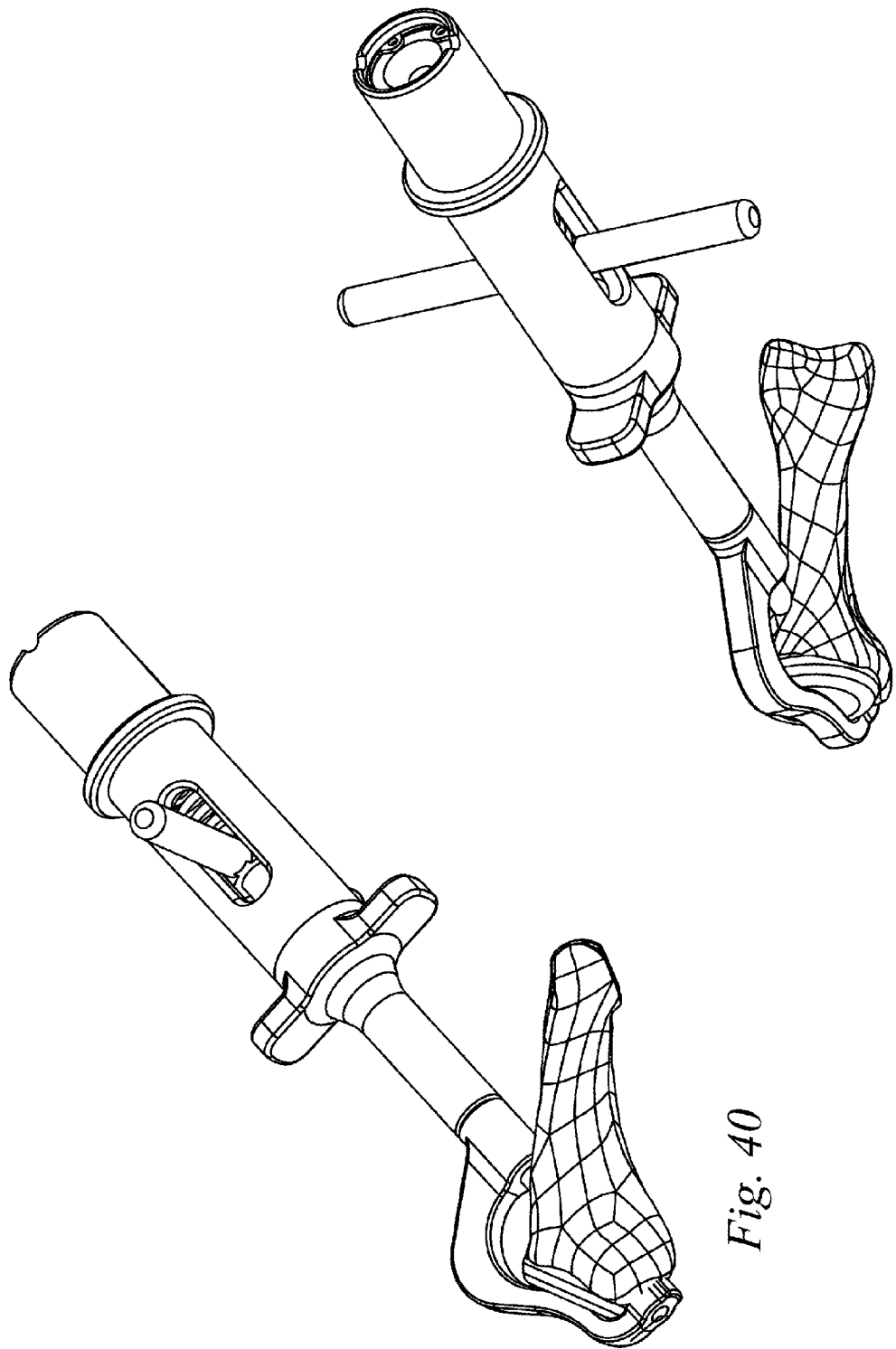

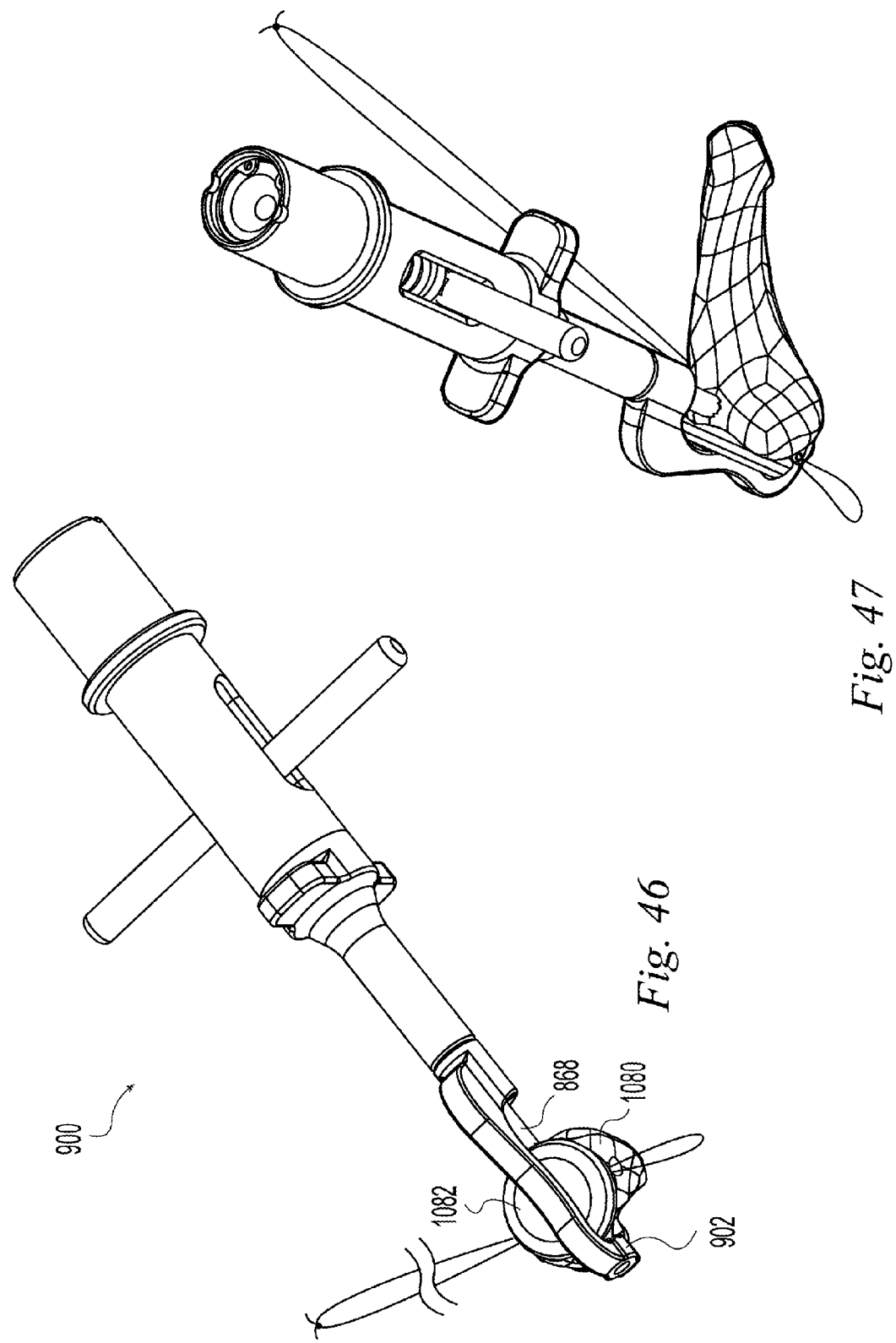

ORTHOPEDIC SUTURE PASSER AND METHOD

CROSS-REFERENCE TO RELATED APPLICATIONS

This application is a continuation-in-part of U.S. patent application Ser. No. 13/527,648, filed Jun. 6, 2012, and a continuation-in-part of U.S. patent application Ser. No. 13/527,765, filed Jun. 20, 2012, both of which claim the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, U.S. Provisional Application No. 61/506,004, filed Jul. 8, 2011, all of which are herein incorporated by reference.

FIELD OF THE INVENTION

The invention relates to devices and methods to pass a suture through material such as, for example, body tissues of a surgical patient and in particular for passing a suture through a bone tunnel in an orthopedic surgical procedure.

BACKGROUND

Various conditions affecting a patient may require surgical intervention involving passing a suture for example to repair a tear, repair an incision, pass grafts, attach grafts, and anchor implants. Various suture passers have been proposed. There is a need for an improved suture passer.

SUMMARY

The present invention provides a suture passer and method to pass a suture through material during a surgical intervention.

In one aspect of the invention, the suture passer includes a guide operable to guide the formation of a tunnel in a bone and guide passage of a suture through the tunnel so formed.

In another aspect of the invention, a suture passer system includes a first suture retriever with a guide and a suture assembly having a suture and a plug connected to the suture. The guide is operable to guide the suture along a guide axis from a first position through an opening in a receiver to a second position in which the plug is constrained from movement toward the first position.

In another aspect of the invention, the suture passer system includes a cutter engageable with the guide. The guide is operable to guide the cutter along the guide axis to form a tunnel in a bone.

In another aspect of the invention, the suture retriever includes a clamping mechanism operable to clamp a bone between the guide and receiver.

In another aspect of the invention, the receiver includes a first reference portion and the suture retriever includes a second reference portion between the receiver and guide, the guide axis being oriented relative to the first and second reference portions based on human anatomy relating anatomic landmarks to a desired bone tunnel orientation in the bone.

In another aspect of the invention, the second reference portion is a surface offset radially from the guide axis by a radial offset distance.

In another aspect of the invention, the suture passer system includes a second suture retriever having a receiver with a first reference portion and a guide aligned with the receiver along a guide axis. The suture second suture retriever further including a second reference portion between the receiver and guide and offset radially from the guide axis by a radial offset distance. The radial offset distance of the first suture retriever is greater than the radial offset distance of the second suture retriever.

In another aspect of the invention, a method includes positioning a receiver of a first suture retriever at a first position on a bone adjacent a bone joint; guiding a cutter with the suture retriever along a guide axis to form a tunnel through the bone aligned with the receiver; guiding a suture with the suture retriever along the guide axis to pass a first portion of the suture through the bone tunnel until the first portion of the suture is received by the receiver; retaining the first portion with the receiver; and moving the receiver away from the first position to advance the suture relative to the bone tunnel.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2 is an exploded perspective view of an illustrative example of a suture passer according to the present invention;

FIG. 3 is a front elevation view of a component of the suture passer of FIG. 2;

FIG. 4 is a top plan view of the component of FIG. 3;

FIG. 5 is a side elevation view of the component of FIG. 3;

FIG. 7 is a perspective view of a component of the suture passer of FIG. 2;

FIG. 8 is an enlarged perspective view of the distal end of the component of FIG. 8;

FIG. 9 is an enlarged perspective view of the proximal end of the component of FIG. 8;

FIG. 21 is a perspective view of an optional component useable with the suture passers of FIG. 1 and FIG. 2;

FIG. 22 is a side elevation view of an alternative suture useable with the suture passers of FIG. 1 and FIG. 2;

FIG. 23 is a side elevation view of an alternative suture useable with the suture passers of FIG. 1 and FIG. 2;

FIG. 24 is a side elevation view of an alternative stopper useable with the sutures of FIG. 1 and FIG. 2;

FIG. 25 is a side elevation view of an alternative stopper useable with the sutures of FIG. 1 and FIG. 2;

FIG. 33 is an exploded perspective view of an illustrative example of a suture shuttle assembly useable with suture passers according to the present invention;

FIG. 34 is an enlarged perspective view of the distal end of the suture shuttle assembly of FIG. 33;

FIG. 35 is a perspective view of the suture shuttle assembly of FIG. 33;

FIG. 36 is a sectional view of the assembly of FIG. 35;

FIG. 37 is a sectional view of the assembly of FIG. 35 oriented 90 degrees from the view of FIG. 36; and FIGS. 38-50 illustrate the suture passers of FIGS. 28 and 30 and the suture shuttle assembly of FIG. 33 in use to pass sutures through a bone.

DESCRIPTION OF THE ILLUSTRATIVE EXAMPLES

The following illustrative examples depict instruments and techniques to pass a suture through a material. Instruments and techniques according to the present invention may be used to pass a suture through any material, at surgical sites anywhere in a patient's body, and for any purpose. Instruments and techniques according to the present invention are particularly useful to pass a suture through a bone tunnel in an orthopedic procedure. For example, it is often desirable to pass a suture through a bone tunnel which in turn is used to pass a graft into the tunnel or attach a graft in the tunnel. While suture passers in accordance with the present invention may be used with any material at any location, and in particular with any bone adjacent any joint within a patient's body, the illustrative examples are shown in use with a small bone joint such as in a hand or foot to form a tunnel in and pass a graft into a metacarpal or metatarsal bone. In particular, the illustrative examples are shown in use with a phalanx bone of the foot. The terms "suture" and "suture strand" are used herein to mean any strand or flexible member, natural or synthetic, able to be passed through material and useful in a surgical procedure. For example, sutures may include, but are not limited to, monofilament, multifilament, strand, tape, and other structures and polymers, metals, and other compositions. The term "material" is used herein to mean implants, grafts, fabric, tendon, ligament, fascia, skin, muscle, bone, and any other material through which it is desirable to pass a suture. The term "transverse" is used herein to mean crossing as in non-parallel. The term "bight" is used herein to mean a bend or loop formed in the intermediate portion of a suture.

Figure 1:
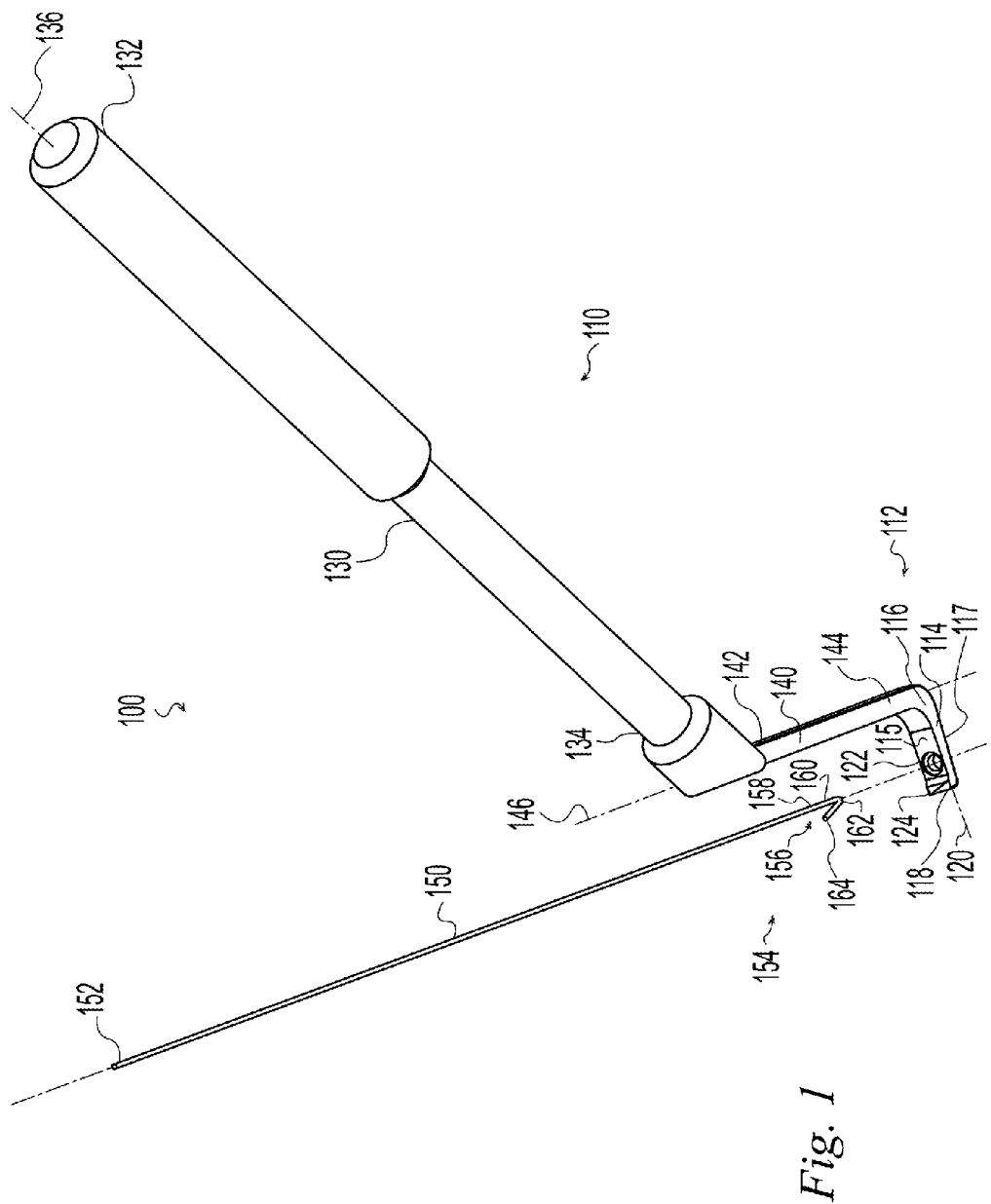
FIG. 1 is an exploded perspective view of an illustrative example of a suture passer according to the present invention.
Figure 6:
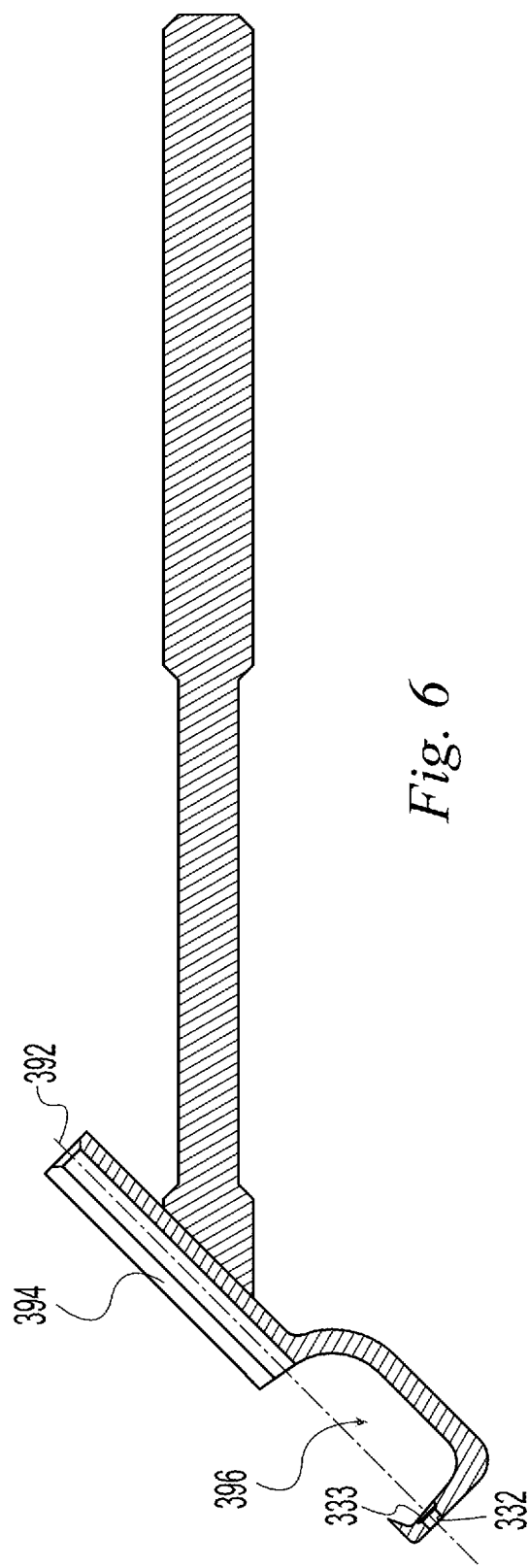
FIG. 6 is a sectional view taken along line 6-6 of FIG. 4.

FIG. 1 depicts an illustrative example of a suture passer 100. The suture passer 100 includes a suture retriever 110 and a suture 150. The retriever 110 includes a receiver 112 able to receive and retain a portion of the suture 150. In the illustrative example of FIG. 1, the receiver 112 includes a foot 114 positionable on one side of a material through which the suture is to be passed. The foot 114 has a proximal end 116, a distal end 118, a front surface 115, a back surface 117 and a longitudinal axis 120 extending between the proximal and distal ends. The foot has an opening 122 defining a passage through a portion of the receiver for receiving the suture 150 and a sharp tip 124 able to engage the material and aid in maintaining the foot 114 in a desired location. In the illustrative example of FIG. 1, the retriever 110 further includes a handle 130 having a proximal end 132, a distal end 134, and a longitudinal axis 136 extending between the proximal and distal ends. The receiver 112 may be mounted directly to the distal end 134 of the handle. In the illustrative example of FIG. 1, the receiver 112 is offset from the handle. An extension 140 having a proximal end 142, a distal end 144, and a longitudinal extension axis 146 extends away from the distal end 134 of the handle transverse to the handle axis 136. The foot 114 is mounted to the distal end 144 of the extension 140 and extends away from the extension 140 transverse to the extension axis 146.

The suture 150 includes a proximal end 152 and a distal end 154. The distal end includes a stopper 156. In the illustrative example of FIG. 1 the stopper 156 includes a hook 158 formed on the distal end 154. For example, the distal end may be bent, molded, heat set, or otherwise formed into a hook shape. The hook 158 includes a shank 160, a bend 162, and a barb 164. The hook 158 is receivable in the opening 122. As the hook 158 is advanced through the opening 122, the barb 164 and shank 160 engage the sides of the opening 122 and the barb 164 moves toward the shank 160. This movement changes the orientation of the hook to a receivable orientation in which the barb-shank maximum dimension is smaller than the opening 122 maximum dimension and the hook passes through the opening. Once the hook 158 is through the opening 122, the barb 164 springs away from the shank 160 and the hook orientation changes to a retention orientation. Pulling the hook 158 back toward the opening causes the barb 164 to engage the back surface 117 of the foot and resist withdrawal. The bend of the hook 158 is such that relatively small movement of the barb 164 is necessary for insertion of the hook through the opening 122 but relatively large movement of the barb 164, in the opposite direction, is necessary for removal. The hook 158 may be withdrawn by forcing the barb to straighten or by clipping the hook 158 off of the suture 150.

The stopper 156 may include any radially extending resilient portion that can catch in the opening 122 or on the back surface 117 of the foot or elsewhere to resist proximal withdrawal of the stopper away from the foot. For example the stopper 156 may include an elastic material, such as nitinol wire, with a hook, bulge, loop, or other feature that resists proximal withdrawal of the stopper away from the foot.

The proximal end of the suture may be unmodified or it may include a loop, knot, hook, barb, or other feature for engaging another material.

In use, the receiver 112 is positioned behind material through which the suture 150 is to be passed. The distal end 154 of the suture is advanced through the material and the stopper 156 is engaged with the receiver 112. The receiver 112 is then withdrawn from behind the material to advance the suture further and retrieve it partially or fully through the material. The suture 150 may be used to connect the material to another material. For example the suture 150 may be used to attach soft tissue to bone. The suture 150 may be used to retrieve something through the material. For example, the suture 150 may be used to retrieve a graft through a bone tunnel. In the illustrative example of FIG. 1, the foot 114 may be positioned adjacent a bone with the opening 122 aligned with a tunnel formed in the bone and the tip 124 engaged with the bone. The distal end 154 of the suture 150 may be advanced through the bone tunnel and opening 122 until the hook 158 engages the foot 114. The proximal end 152 of the suture may be secured to a graft such as by tying, stitching, looping, knotting, hooking, or other securing mechanism. The foot may then be withdrawn away from the bone tunnel to retrieve the distal 154 end of the suture and pull the graft with it. Further pulling of the suture advances the graft into the bone tunnel.

FIGS. 2-9 depict an illustrative example of a suture passer 200 similar to that of FIG. 1 and including a suture retriever 300 and a suture 400. In the illustrative example of FIGS. 2-9, the suture retriever 300 includes a handle 310, a receiver 320, and a guide 380. The handle 310 includes a proximal end 312, a distal end 314, and a longitudinal axis 316 extending between the proximal and distal ends. The receiver 320 includes a foot 324 positionable on one side of a material through which the suture is to be passed. The foot 324 has a proximal end 326, a distal end 328, a front surface 325, a back surface 327 and a longitudinal axis 330 extending between the proximal and distal ends. The foot 324 has an opening 332 having an opening axis and able to receiving the suture 400. The opening 332 includes an enlarged counterbore 333. The foot further includes a sharp tip 334 able to engage the material and aid in maintaining the foot 324 in a desired location. The receiver 320 is offset from the handle 310. An extension 340 having a proximal end 342, a distal end 344, and a longitudinal extension axis 346 extends away from the distal end 314 of the handle transverse to the handle axis 316. The foot 324 is mounted to the distal end 344 of the extension 340 and extends away from the extension 340 transverse to the extension axis 346.

The guide 380 includes a tube 382 having an inner surface 384, an outer surface 386, a proximal end 388, and a distal end 390. The inner surface 384 defines an inner diameter and a longitudinal axis 392. The tube 382 is mounted to the distal end 314 of the handle 310 with the tube axis 392 transverse to the handle axis 316 and coaxial with the opening 332 in the foot 324. The handle 310 axis 316 forms an angle 317 with the tube axis 392. The angle 317 facilitates manipulating the retriever 300 while maintaining a line of sight for the user and to prevent interference with tissues surrounding the surgical site. The angle 317 may have any suitable value. Preferably the angle 317 is in the range of 90 to 270 degrees. The handle 310 may also be mounted at any location around the circumference of the tube 382. In the illustrative embodiment of FIGS. 2-9, the handle is coplanar with the foot 324. The tube 382 includes a slot 394 through the sidewall of the tube from the inner surface 384 to the outer surface 386 and extending from the proximal end 388 to the distal end 390. The guide 380 and foot 324 define a space 396 between them for receiving a bone.

The suture 400 includes a proximal end 402 and a distal end 404. The distal end includes a stopper 406. In the illustrative example of FIGS. 2-9 the stopper 406 includes a pledget 408. The pledget 408 is mounted to the suture 400 such as by adhering, welding, crimping, molding or other suitable mounting method. The pledget 408 may also be formed as a unitary part of the suture. The pledget is resilient to allow it to bend or compress to fit through the opening 332. It may also be toggled to one side such as for example by bending the suture adjacent the pledget 408 to fit through the opening 332. In the illustrative example of FIGS. 2-9, the pledget 408 includes radially extending tabs 410, 412 that bend from substantially perpendicular to the suture 400 to substantially parallel to the suture 400 to reduce the radial dimension of the pledget 408 and allow it to pass through the opening in a receivable orientation. Once the pledget 408 is through the opening 332, the tabs 410, 412 spring back to their initial position and resume a retention orientation. The proximal end of the suture 400 includes a loop 420. The loop may be formed by tying a knot in a bight of a single or multiple strand suture 400, tying the ends of multiple strands together, splitting a monofilament strand, molding, or other suitable loop formation method. In the illustrative example of FIGS. 2-9, the loop is formed by molding a loop on a monofilament strand.

Figure 10:
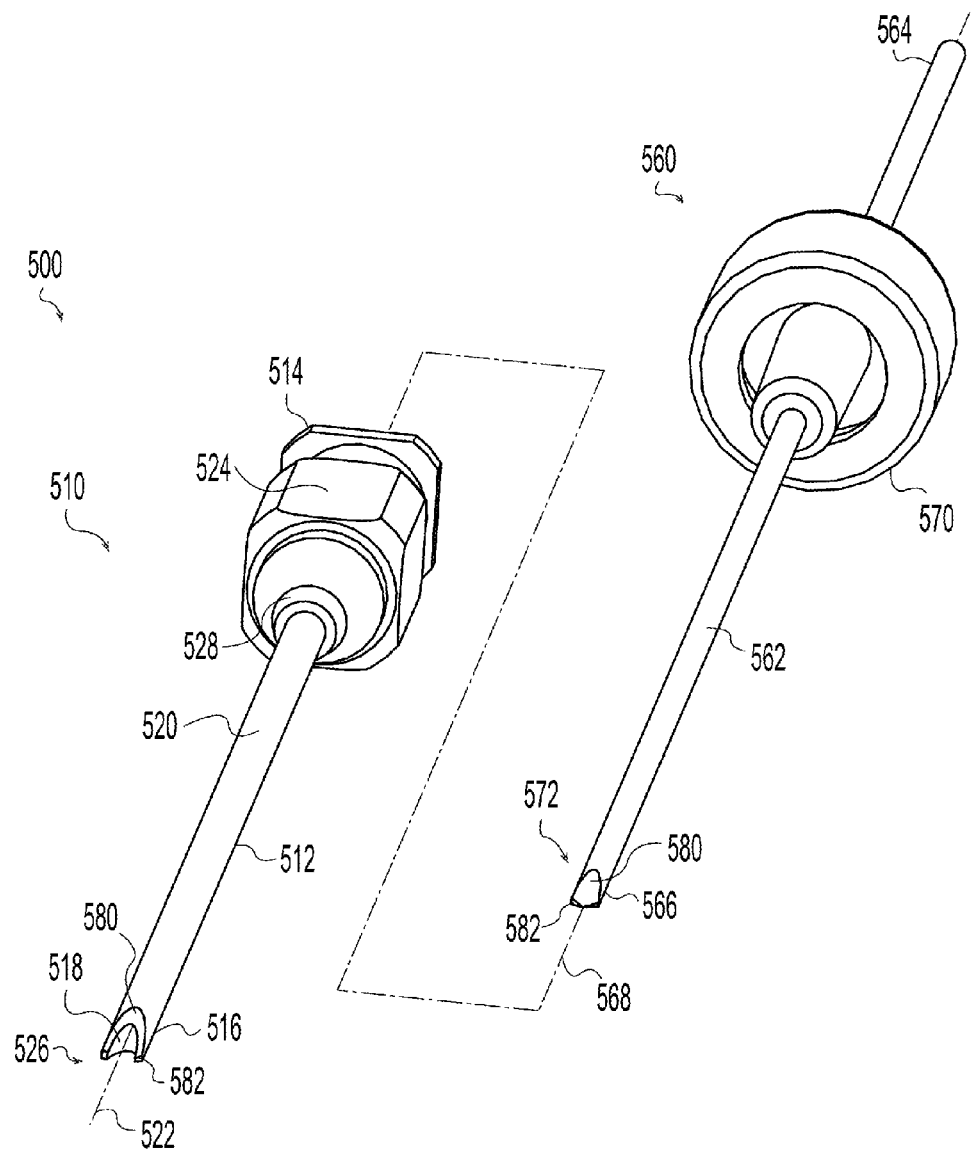
FIG. 10 is a perspective view of a drill assembly useable with the suture passer of FIG. 2.

FIG. 10 illustrates a drill assembly 500 useable with the suture passer 200. The drill assembly 500 includes a drill tube 510 and an obturator 560. The drill tube 510 includes a tubular body 512 having a proximal end 514, a distal end 516, an inner surface 518, and an outer surface 520. The inner surface 518 defines an inner diameter and a longitudinal axis 522 extending between the proximal and distal ends. In the illustrative embodiment of FIG. 10, a connector 524 is mounted to the drill tube 510 near the proximal end 514. In the illustrative example of FIG. 10, the connector 524 is a female Luer-type fitting. A stop 528 extends radially outwardly from the body 512.

The obturator 560 includes an elongated body 562 having a proximal end 564, a distal end 566, and a longitudinal axis 568 extending between the proximal and distal ends. In the illustrative embodiment of FIG. 10, a connector 570 is mounted to the obturator 560 intermediate the proximal and distal ends. In the illustrative example of FIG. 10, the connector 570 is a male Luer-type fitting. The obturator 560 is receivable in the drill tube 510 by inserting the distal end 566 of the obturator 560 into the proximal end 514 of the drill tube 510 and advancing the obturator until the connectors engage. The obturator 560 and drill tube 510 are locked together by rotating the connectors relative to one another. The drill tube 510 and obturator 560 have drilling tips 526, 572 that align when the obturator is inserted into the drill tube and locked. For example, the drilling tips 526, 572 may be formed by assembling the obturator 560 and drill tube 510, locking them together, and then grinding the cutting tips on the drill tube 510 and obturator 560 simultaneously. In the illustrative example of FIG. 10, when the drill tube 510 and obturator 560 are assembled, the drilling tips 526, 572 form a diamond drill tip having primary bevels 580 formed on opposed first and second sides and secondary bevels 582 to provide relief and improve cutting. The outer diameter of the drill tube 510 and the counterbore 333 of the opening 332 are sized so that the drill tube 510 may be received in the counterbore 333.

Figure 11:
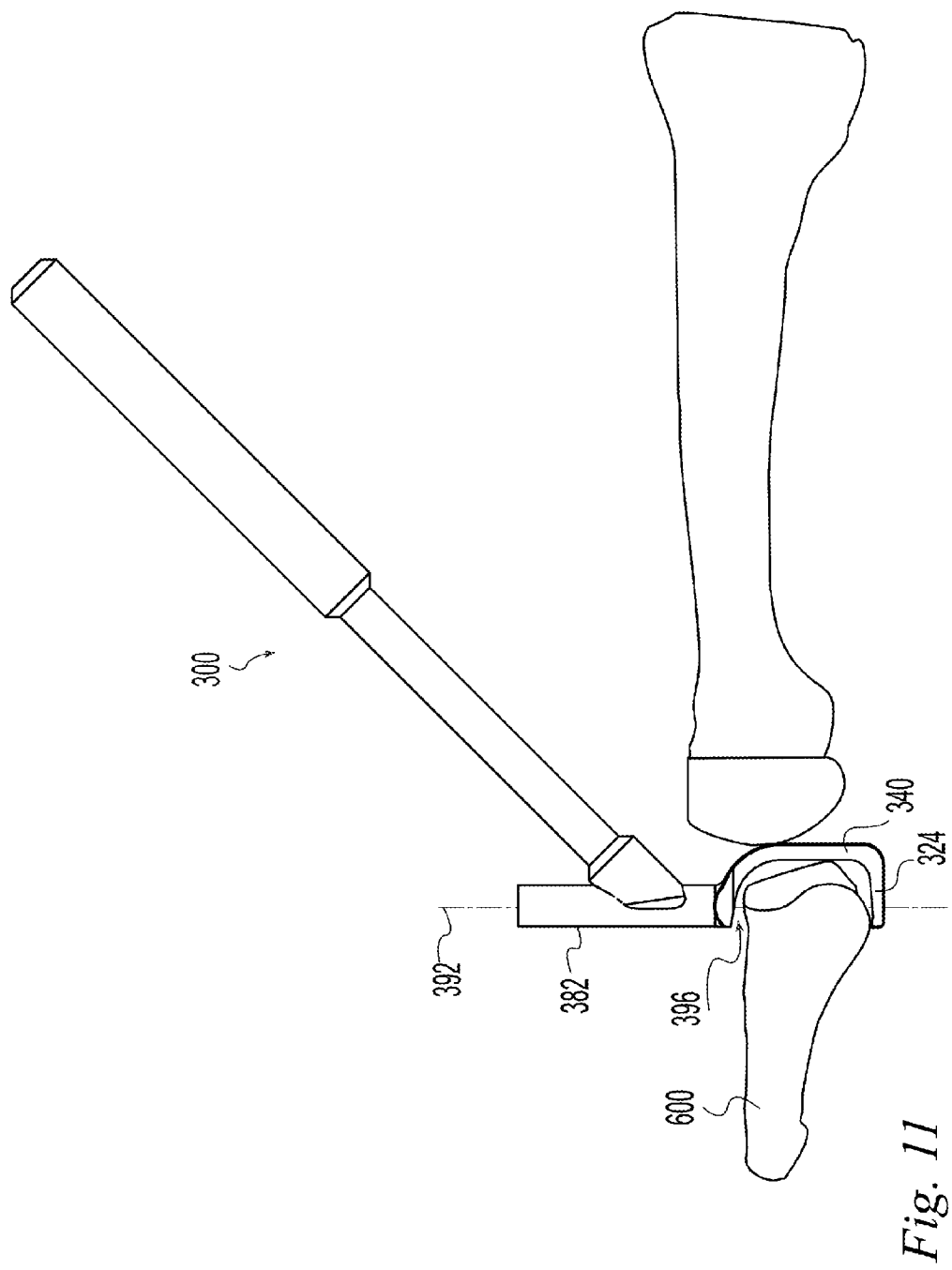
FIGS. 11-20 are side elevation views illustrating the suture passer of FIG. 2 in use.

FIGS. 11-20 illustrate the illustrative suture passer 200 of FIGS. 2-9 and the illustrative drill assembly of FIG. 10 in use to form a bone tunnel and load a graft into the tunnel. In FIG. 11, the suture retriever 300 has been positioned adjacent a bone 600 with the foot 324 on one side of the bone with the opening 332 aligned with a desired exit location for a bone tunnel and the guide axis 392 aligned with the desired tunnel axis. By viewing through the tube 382 along the axis 392, the location of the tunnel entrance can be visualized. The retriever 300 is shown positioned adjacent a phalanx bone with the extension 340 in the joint space and the guide positioned to form a tunnel from dorsal to plantar through the proximal phalanx. The guide may be positioned at any location around the joint to create bone tunnels at any desired location in the phalanx or the metatarsus. For example, the guide may be positioned to create tunnels for repairing or replacing a proper collateral ligament, accessory plantar ligament, plantar plate, or other structure in or around the joint.

Figure 12:
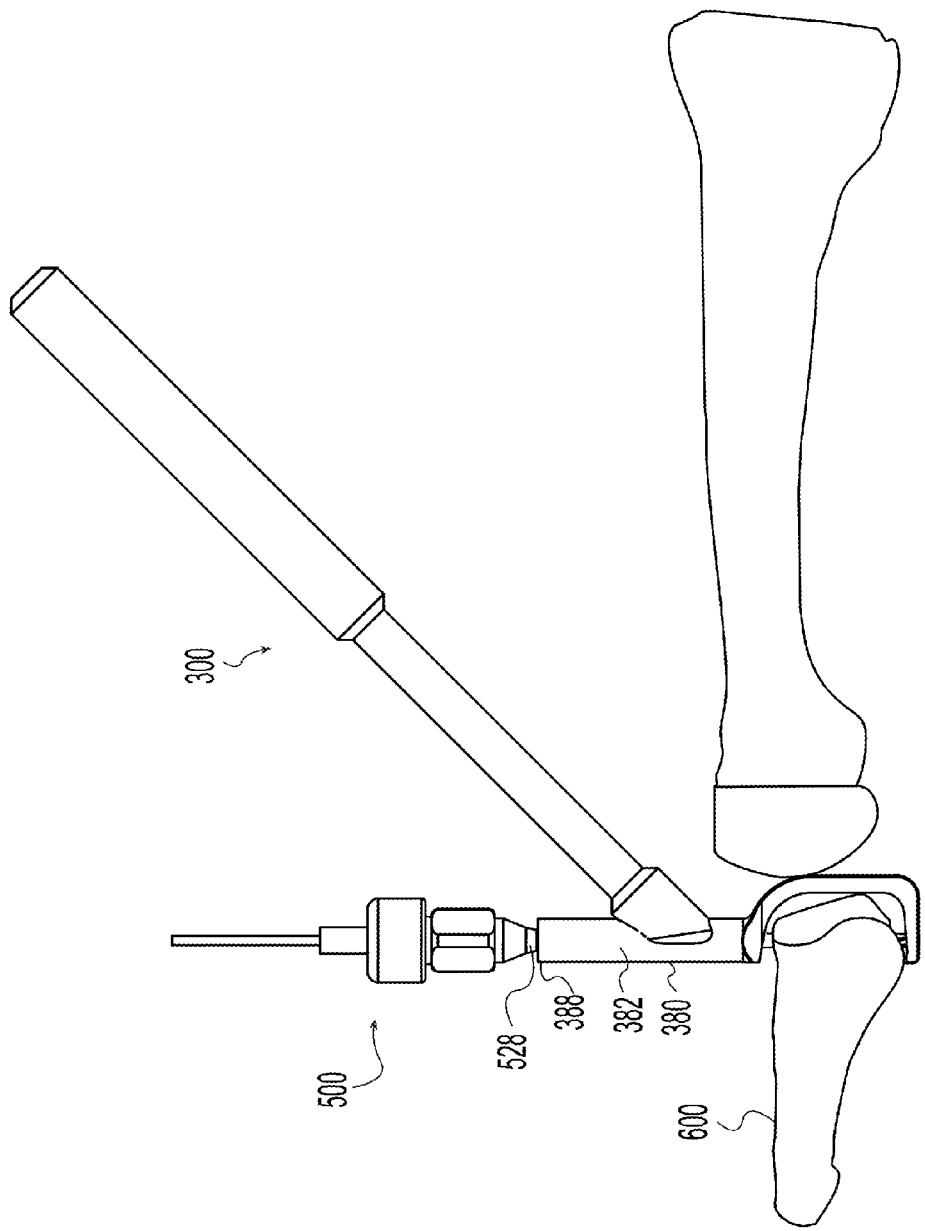

In FIG. 12, the drill assembly 500 has been guided via the inner surface 384 of the guide tube 382 to form a tunnel through the bone 600. Stop 528 abuts the proximal end 388 of the guide 380 to limit the drilling depth. In the illustrative examples of FIGS. 2-10, the stop 528 abuts the proximal end 388 when the drill tube 510 is received in the counterbore 333. Alternatively, the opening in the foot may be sized to engage the tip of the drill to limit the depth or a depth stop may be omitted.

Figure 13:
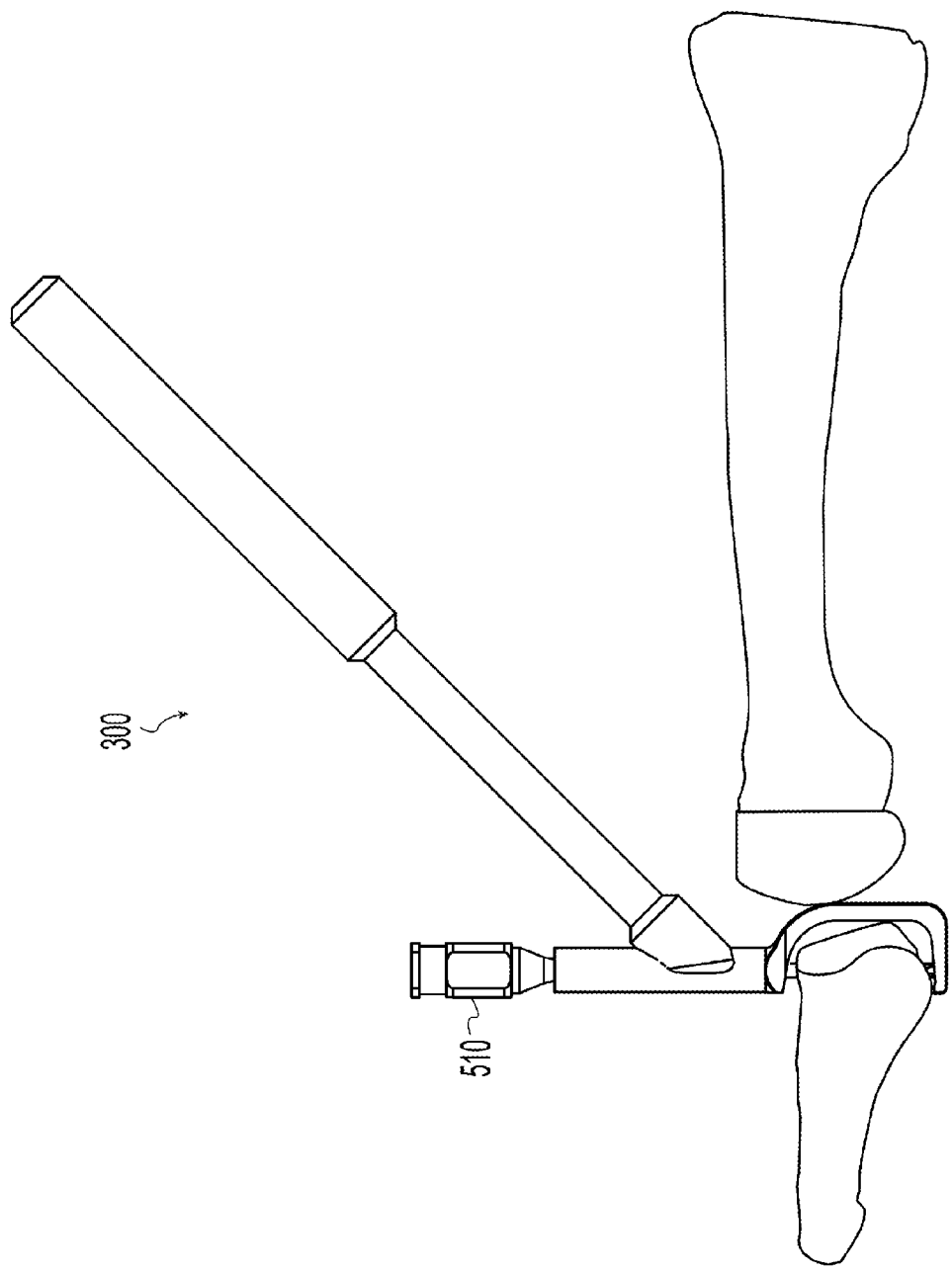

In FIG. 13, the obturator 560 has been removed leaving the drill tube 510 in place. Optionally, the drill tube 510 could be removed or a one-piece drill could be substituted for the drill assembly 500. However, by leaving the drill tube 510 in place, the drill tube 510 locks the retriever 300 in place on the bone, provides guidance for the suture, and provides a smooth passage for the suture.

Figure 14:
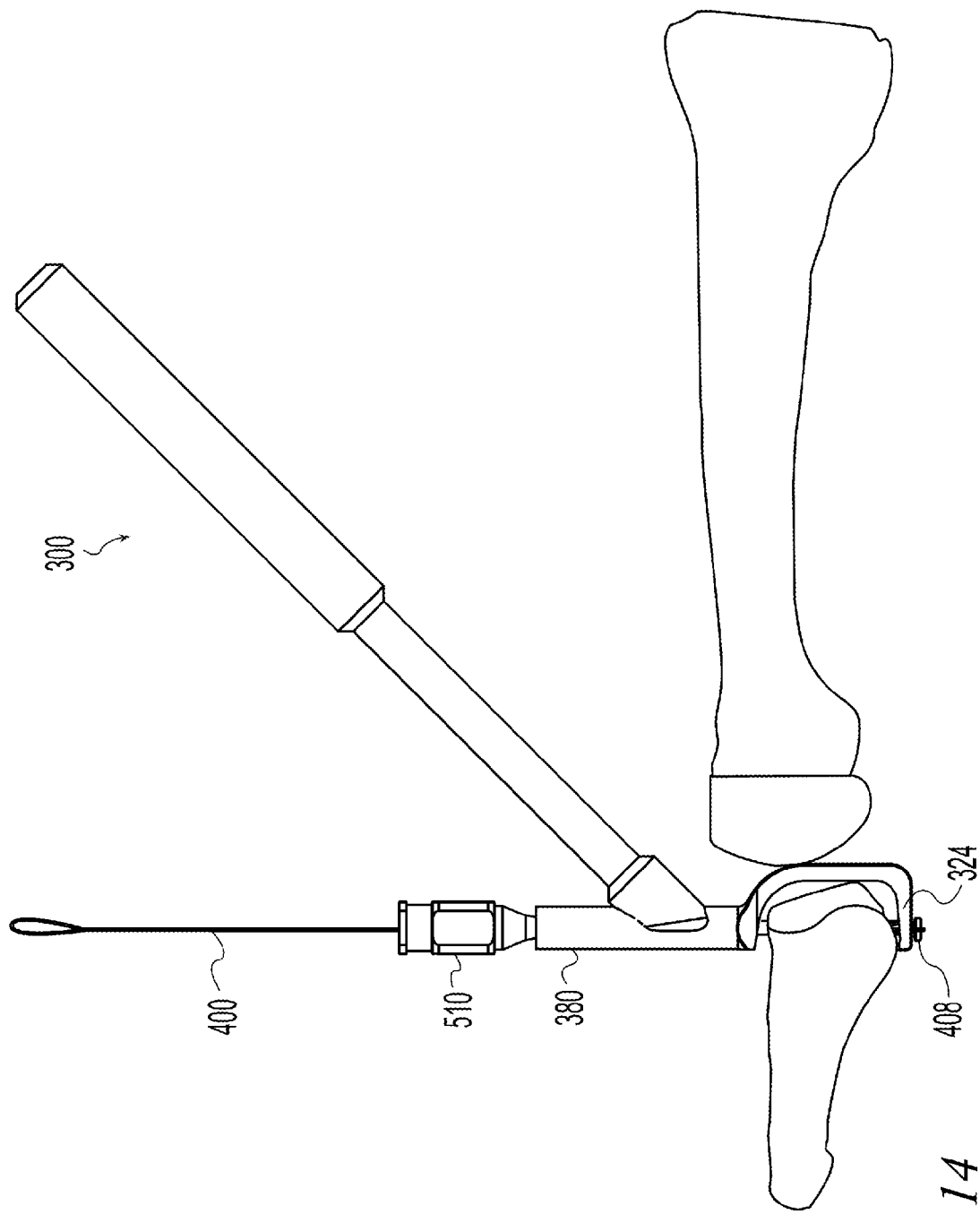

In FIG. 14, the suture 400 has been inserted until the stopper 406 engages the receiver 320. In the example of FIG. 14, the pledget 408 has been forced through the opening 332 in the foot 324.

Figure 15:
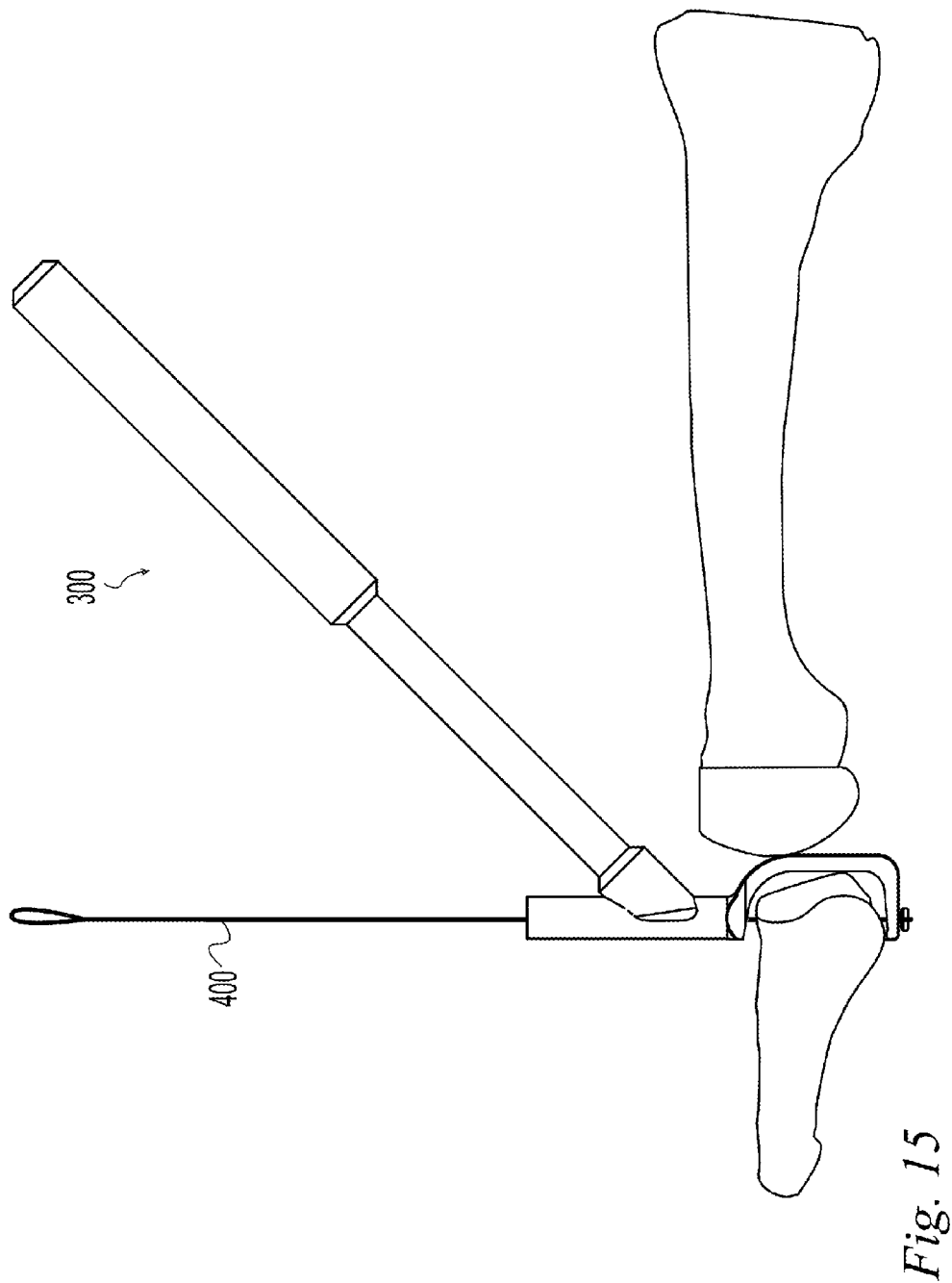

In FIG. 15, the drill tube 510 has been removed leaving the suture 400 in place.

Figure 16:
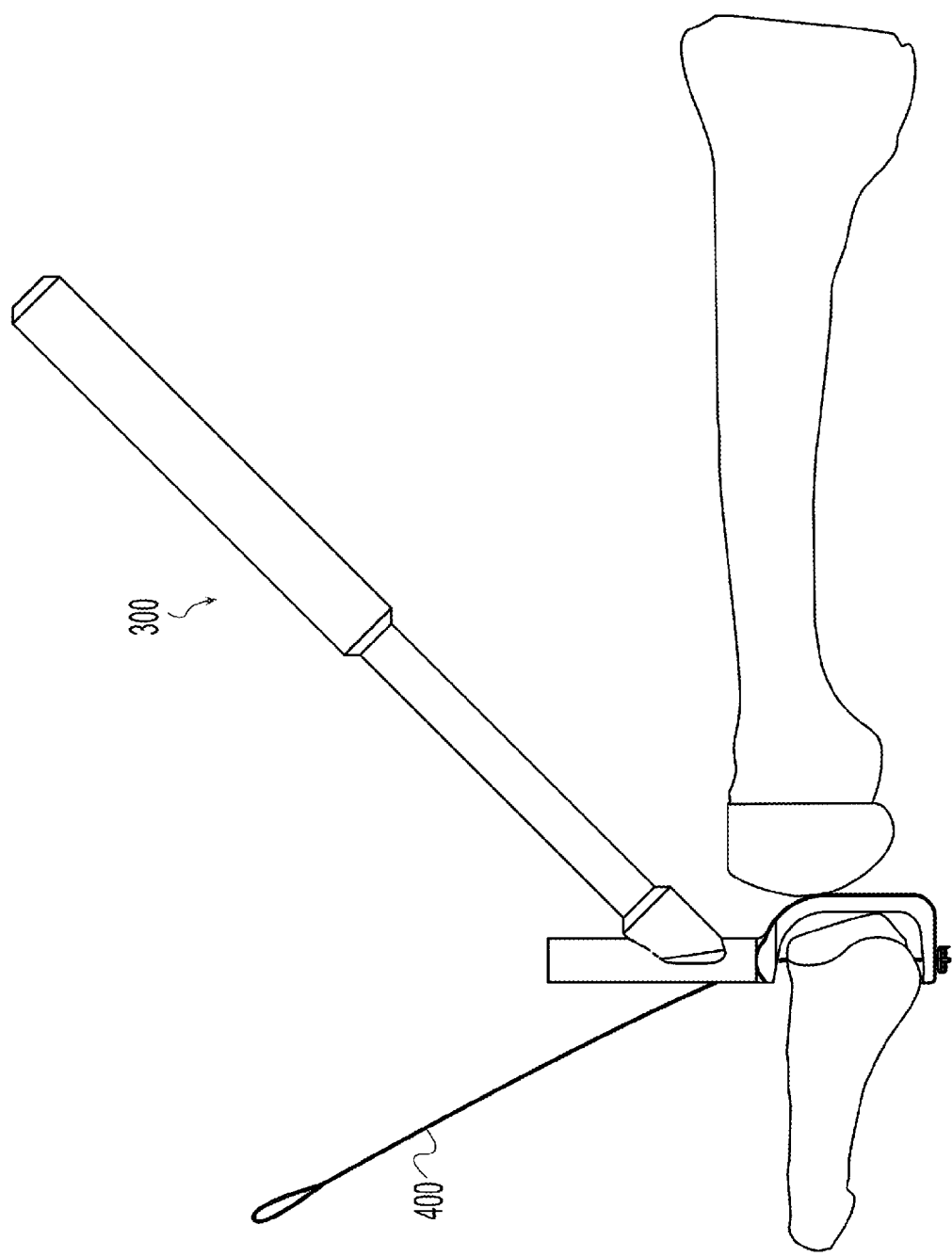

In FIG. 16, the suture 400 has been pulled through the slot 394 to free the proximal end 402 from the guide tube 382. The slot 394 simplifies withdrawing the retriever 300 from the surgical site. However, the slot 394 may be omitted and the proximal end 402 of the suture threaded through the guide tube 382 as the retriever 300 is withdrawn.

Figure 17:
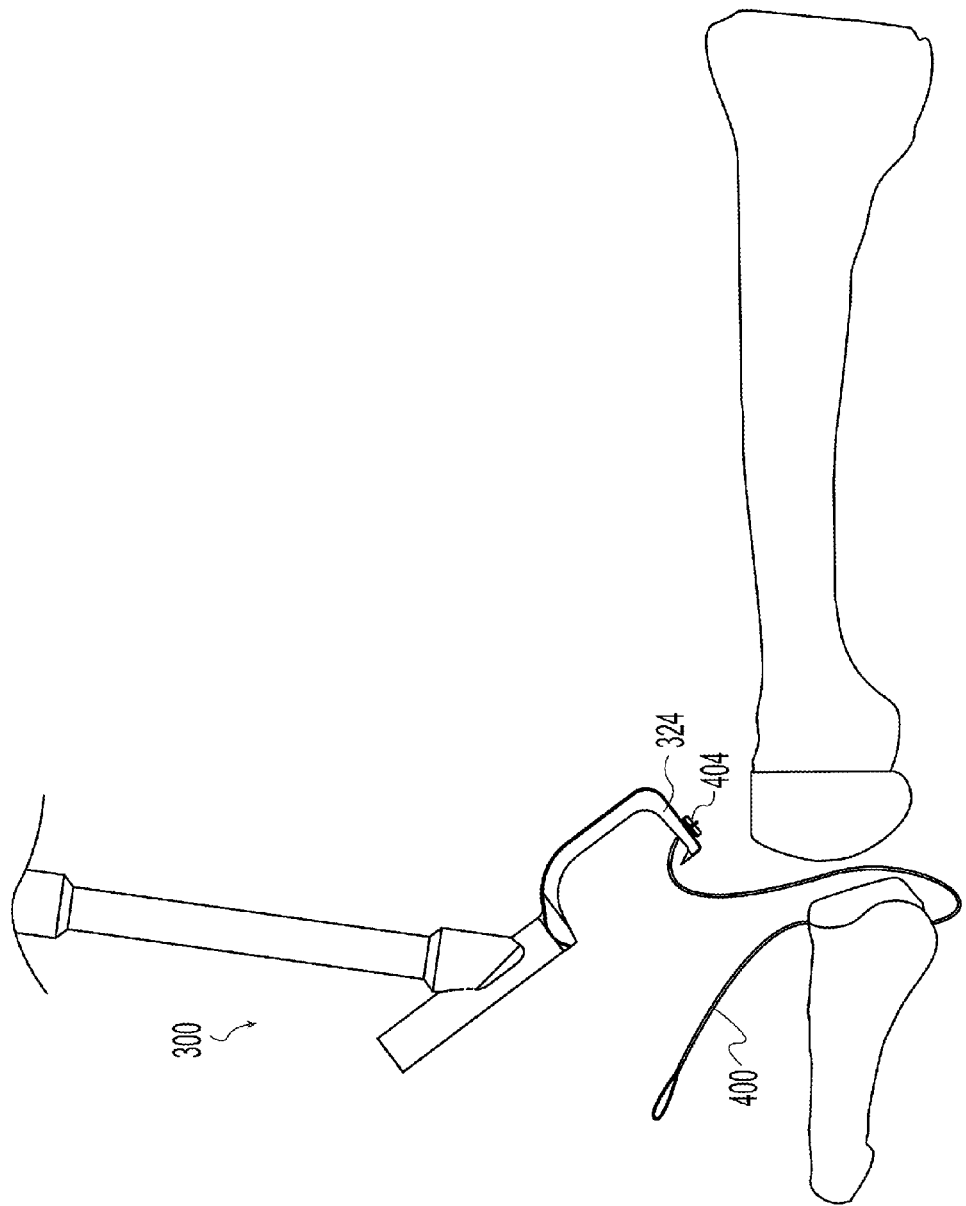

In FIG. 17, the retriever 300 has been withdrawn from the surgical site taking the distal end 404 of the suture 400 with it and thereby further advancing the suture 400 into the bone tunnel. The suture 400 may be left attached to the retriever 300 or it may be separated from the retriever by pulling the distal end 404 back through the foot or cutting off the distal end 404 of the suture.

Figure 18:
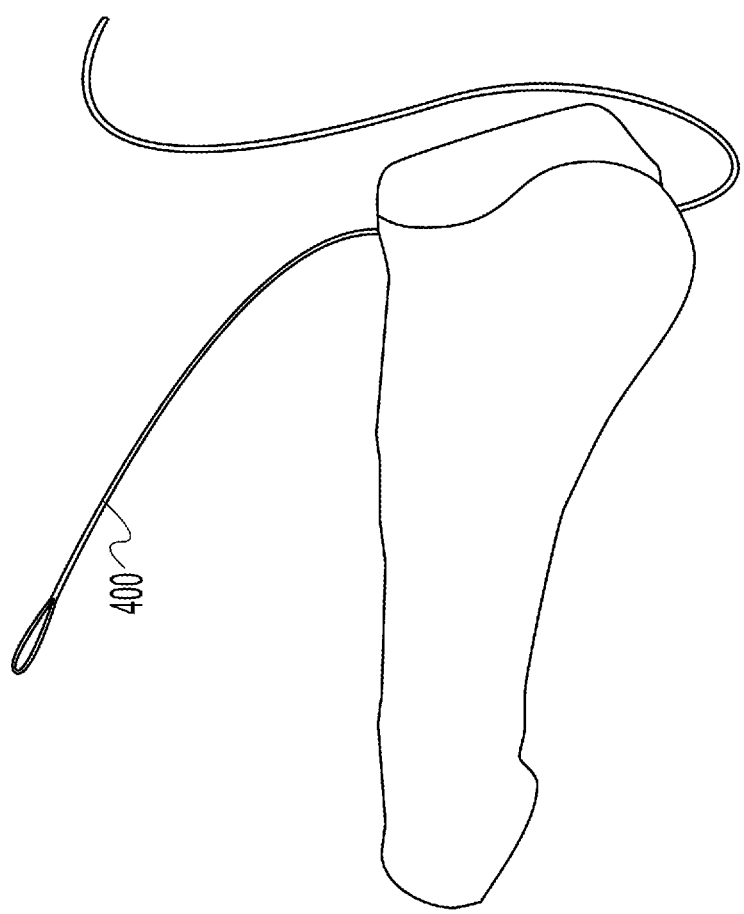

In FIG. 18, the distal end 404 of the suture 400 has been cut off to free it from the retriever 300 and the retriever 300 removed.

Figure 19:
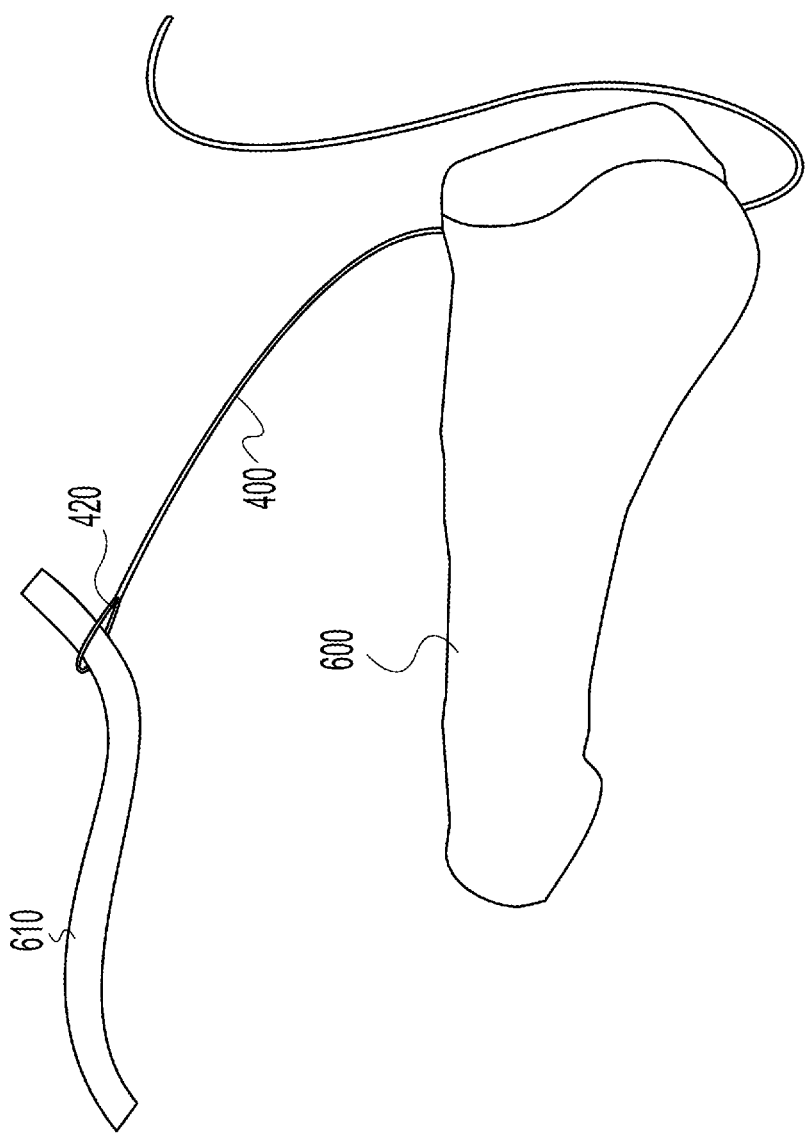

In FIG. 19, a graft 610 has been engaged with the proximal end 402 of the suture 400 by threading it through the loop 420. Alternatively, a graft or any other material may be attached to the distal end for pulling in the opposite direction. In addition to being used to retrieve a graft, the suture 400 may be used as a definitive suture in a repair or reconstruction. Also, the suture 400 may be used to pull another graft retrieval strand such as, for example, a larger or more flexible strand.

Figure 20:
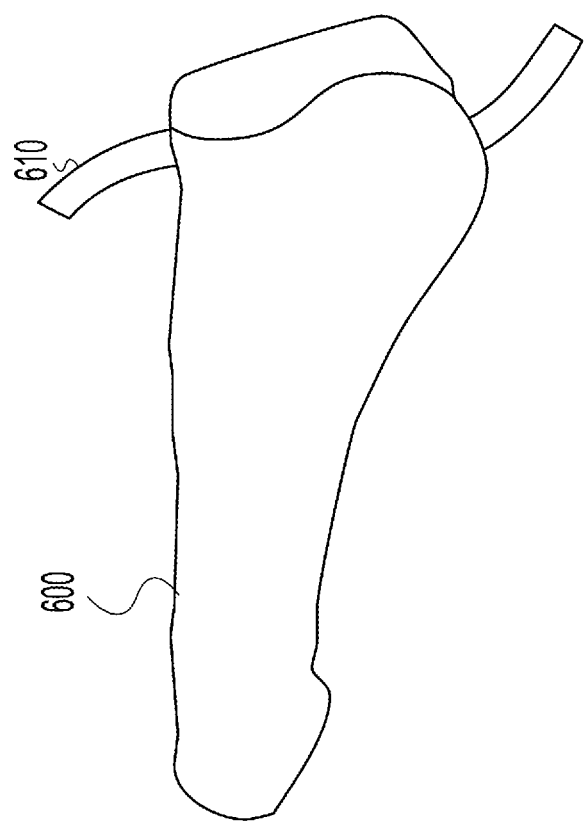

In FIG. 20, the suture 400 has been pulled to advance it through the bone tunnel and pull the graft 610 along with it to position the graft 610 in the bone tunnel and the suture 400 has been removed.

FIG. 21 illustrates a suture inserter 710 having an elongated body 712 with a proximal end 714, a distal end 716, and a longitudinal axis 718. The suture inserter 710 may be used to advance the suture 400 into engagement with the receiver 320 by pushing the stopper 406. The suture inserter 710 or the suture inserter 710 in combination with the suture may have a higher columnar strength than the suture alone and facilitate advancing the suture 400. In the illustrative example, the suture inserter includes a longitudinal passage 720 for receiving the suture 400 with the stopper 406 adjacent the distal end 716.

FIG. 22 illustrates a suture 730 having two strands 732 joined to a stopper 734 having a proximal end 736 formed at an angle to the suture strands 732 so that the proximal end 736 will hook onto the retriever 320. The suture 730 is also shown with the suture inserter 710 of FIG. 21 useable to push the stopper 734. For use in passing a graft, the suture strands 732 may be tied to form a loop, stitched to the graft, wrapped around the graft, or otherwise connected to the graft. The suture ends may also be used directly to attach hard or soft tissue, implants, or other materials at a surgical site. The suture strands may also be used directly as a ligament or tendon replacement.

FIG. 23 illustrates a suture 740 having a loop 742 retained by swaging a ferrule 744 to retain the proximal end 746 of the suture 740.

FIG. 24 illustrates a suture 750 having a stopper 752 formed of a block of resilient material such as, for example, a closed cell foam.

FIG. 25 illustrates a suture 760 having a stopper 762 joined to a strand 764 at a pivot 766 so that the stopper 762 can toggle between a receiving position generally more parallel to the strand 764 and a retaining position generally more perpendicular to the strand 764.

Figure 26:
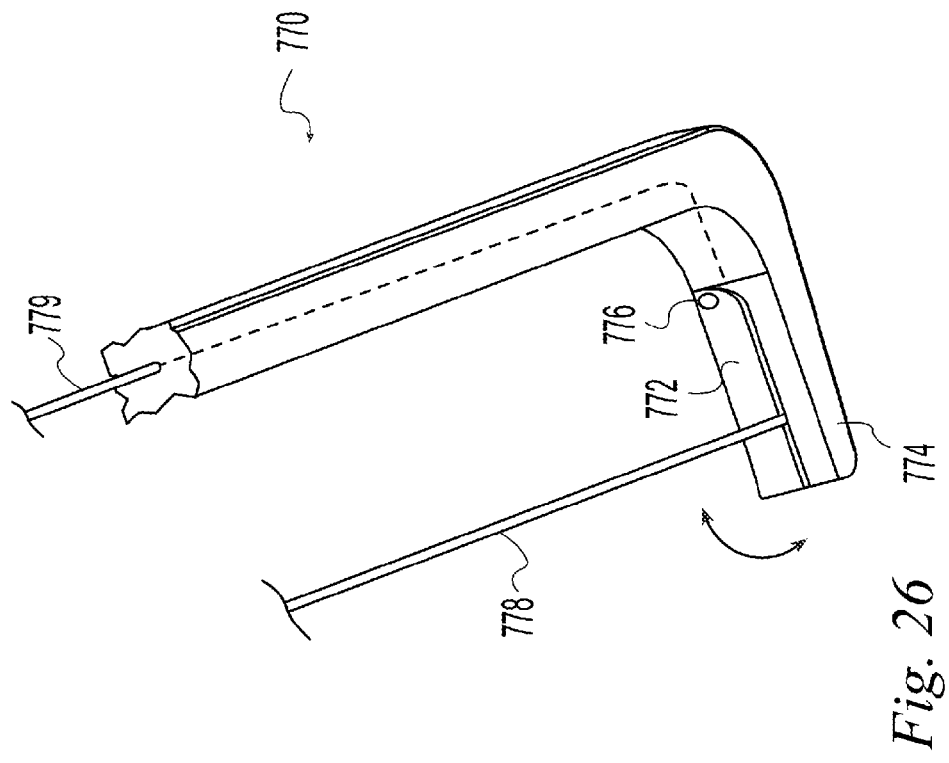
FIG. 26 is a perspective view of an alternative receiver useable with the suture passers of FIG. 1 and FIG. 2.

FIG. 26 illustrates an alternative foot 770 to the foot 224 of FIG. 2. The foot 770 has first and second opposable jaws 772, 774. The first jaw 772 is mounted for rotation relative to the second jaw about a pivot 776. The jaws 772, 774 are moveable between a first closed, position (shown) in which the jaw faces are adjacent one another and a second, open position (not shown) in which the first jaw 772 is pivoted away from the second jaw 774 to create a space between the jaws 772, 774 for receiving a suture 778. The jaws may be closed on the suture 778 to retain the suture and allow it to be retrieved. Any suitable mechanism may be used to move the first jaw relative to the second jaw. For example, a control cable 779 may be mounted in the foot and moveable by a remote actuator to move the first jaw 772 between the first and second positions.

Figure 27:
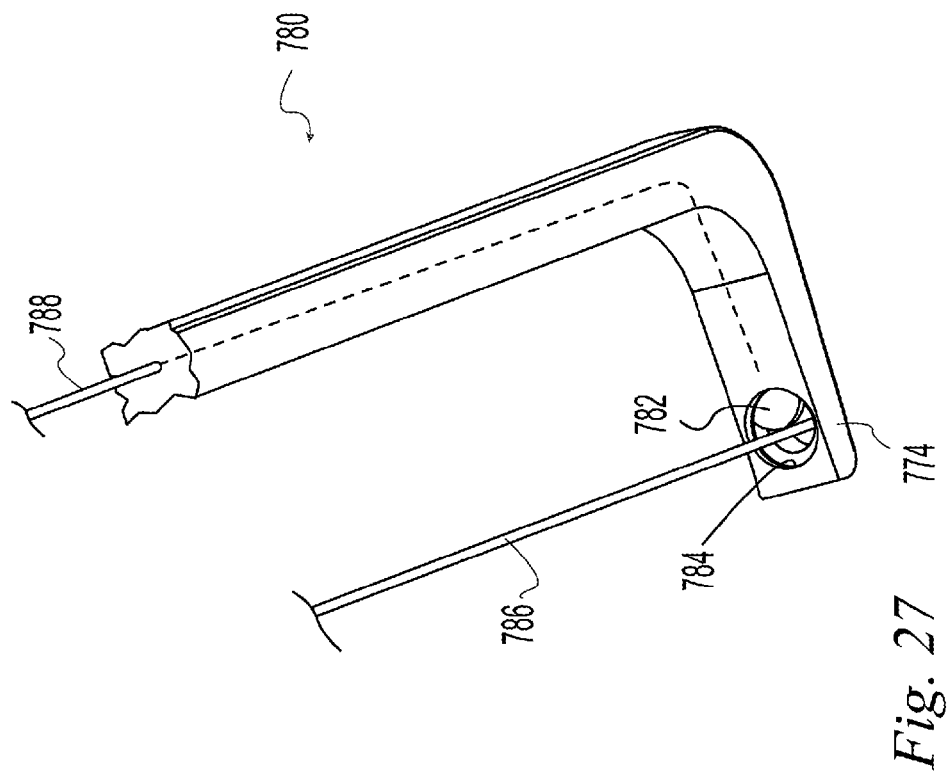
FIG. 27 is a perspective view of an alternative receiver useable with the suture passers of FIG. 1 and FIG. 2.

FIG. 27 illustrates an alternative foot 780 to the foot 224 of FIG. 2. The foot 780 has moveable member 782 mounted for movement relative to an opening 784 between a first position in which the opening is not blocked and a suture 786 may be received in the opening and a second position in which the member 782 and edge of the opening 784 grasp the suture. Any suitable mechanism may be used to move the member 782. For example, a control cable 788 may be mounted in the foot and moveable by a remote actuator to move the member 782 between the first and second positions.

Figure 28:
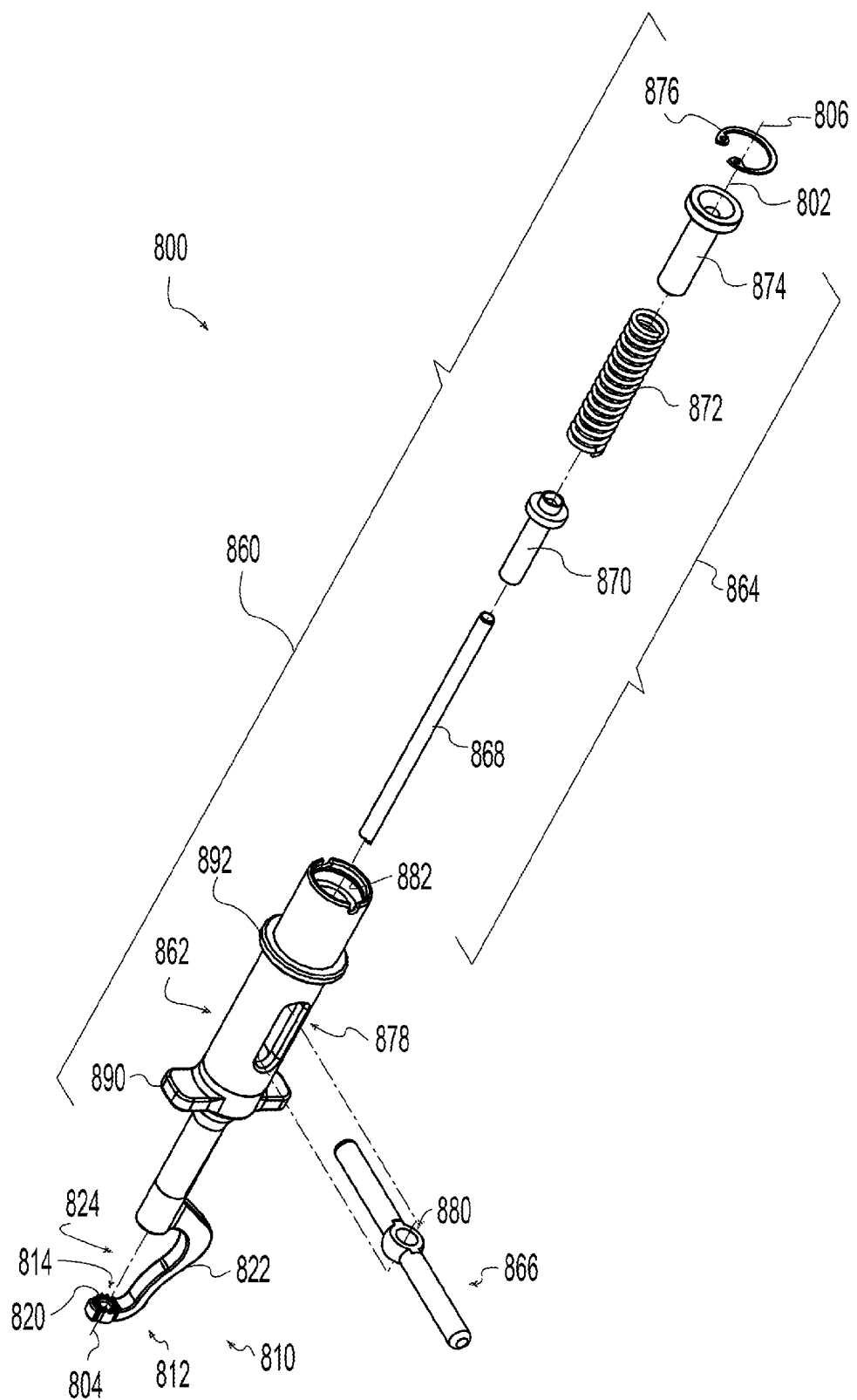
FIG. 28 is an exploded perspective view of an illustrative example of a suture passer according to the present invention.
Figure 29:
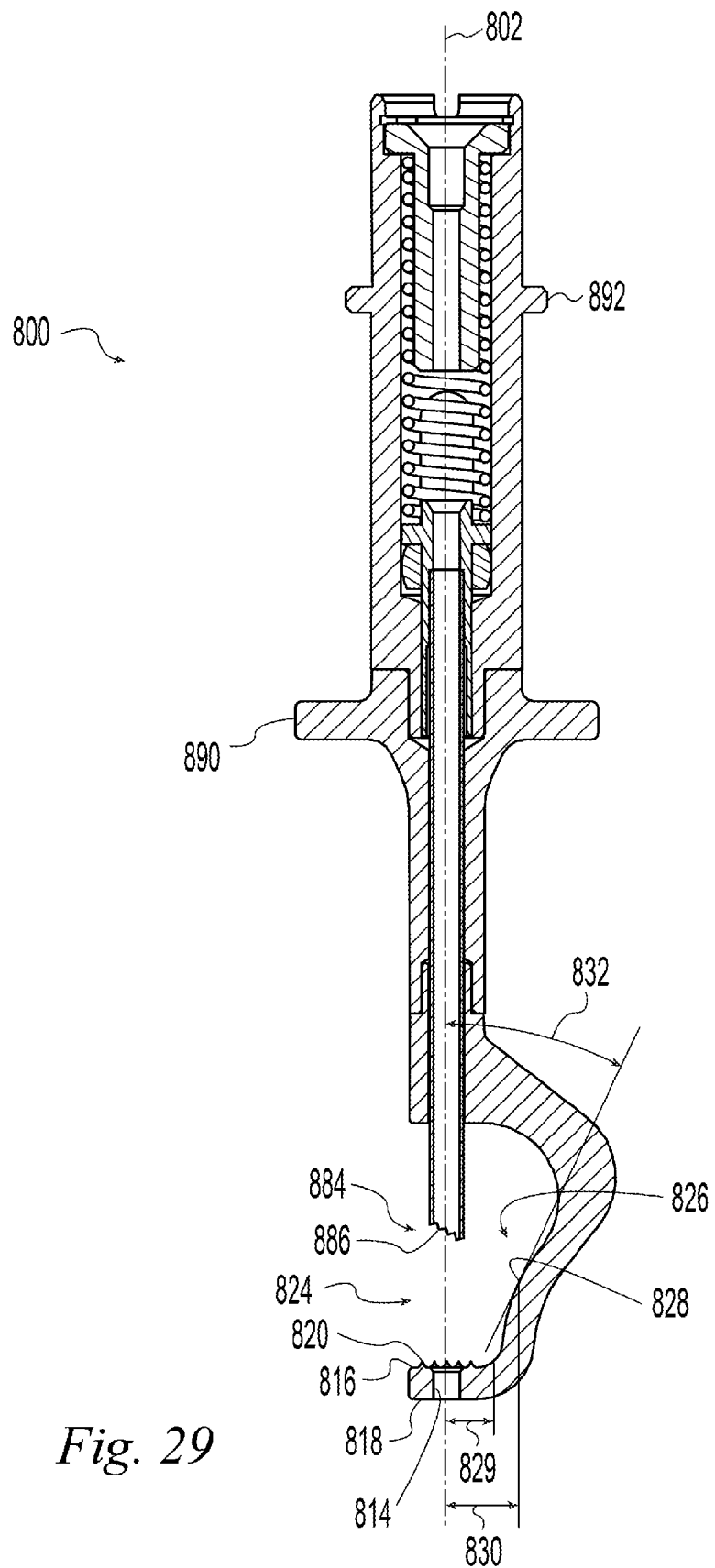
FIG. 29 is a side section view of the suture passer of FIG. 28.
Figure 30:
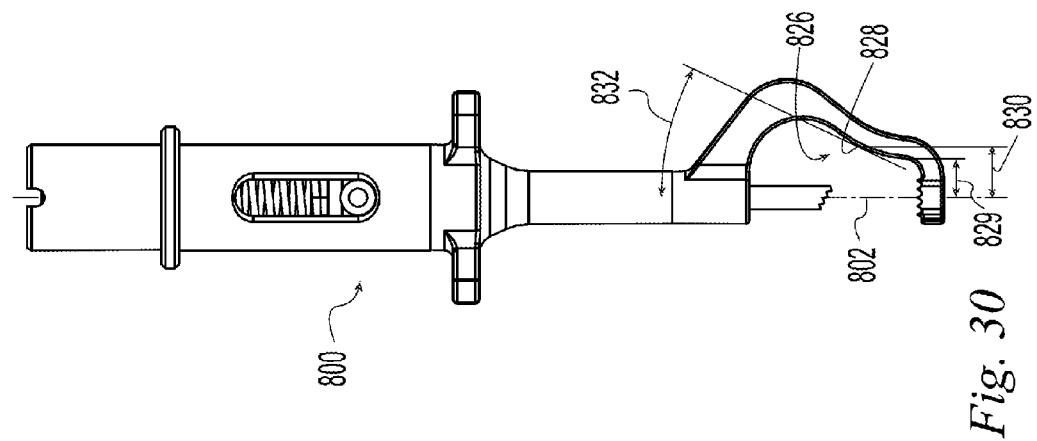
FIG. 30 is a side elevation view of the suture passer of FIG. 28.

FIGS. 28-30 depict an illustrative example of a suture retriever 800. In the illustrative example of FIGS. 28-30, the suture retriever 800 includes a receiver 810 and a guide 860. The receiver 810 and guide 860 are oriented relative to a longitudinal axis 802 extending between distal 804 and proximal ends 806. The receiver includes a foot 812 positionable on one side of a material through which a suture is to be passed. An opening 814 extends through the foot 812 coaxial with the longitudinal axis 802 between a proximal facing surface 816 and a distal facing surface 818 of the foot 812. The foot 812 further includes a plurality of teeth 820 able to engage the material and aid in maintaining the material and the foot in a desired location. The foot is connected to the guide 860 by an extension 822. The extension 822 is offset radially from the longitudinal axis 802 to define a space 824 for receiving material, such as for example a bone. In the illustrative example of FIGS. 28-30, the proximal facing surface 816 of the foot 812 is sized to engage a desired location for a bone tunnel exit and the extension 822 is shaped to engage the articular surface of a phalangeal bone such as of a human hand or foot. The offset of the extension 822 from the longitudinal axis 802 varies proximally and distally. In the illustrative example of FIGS. 28-30, the offset distance 829 adjacent the proximally facing surface 816 of the foot is in the range of 1-4 mm. Preferably, the offset distance 829 is approximately 2 mm. This offset corresponds to the distance from the edge of the articular surface of the proximal phalanx to the anatomic insertion site of the plantar plate on the plantar aspect of the proximal phalanx of a human foot. Other offset distances may be used for other anatomic sites. The extension 822 has a curved articular surface engaging portion 826 that is convex toward the longitudinal axis 802. The articular surface engaging portion 826 defines an apex 828 that is radially offset from the longitudinal axis 802 by a radial offset distance 830. The articular surface engaging portion 826 is angled relative to the longitudinal axis such that a tangent line through the apex 828 and coplanar with the longitudinal axis 802 forms an angle 832 with the longitudinal axis. The proximal facing surface 816 of the foot, the articular surface engaging portion 826 of the extension, and the longitudinal axis 802 are oriented relative to one another based on human anatomy relating anatomic landmarks to a desired bone tunnel orientation in the bone. For example, with the proximal facing surface of the foot 816 engaging a ligament insertion on the proximal phalanx and the articular surface engaging portion 826 engaging the center of the articular surface of the proximal phalanx at the metatarsophalangeal joint, the longitudinal axis 802 will be directed along a desired bone tunnel path.

The guide 860 includes a hollow body 862 containing a clamping and guiding mechanism 864. The mechanism 864 includes a handle 866, a tube 868, a lower spring guide 870, a spring 872, an upper spring guide 874, and a retaining clip 876 all coaxially aligned with the longitudinal axis 802. The guide 860 is assembled by first inserting the tube 868 into the lower spring guide and securing it for example by press fitting, welding, bonding, or other suitable means. Next the handle 866 is inserted through elongated openings 878 in the side of the body 862 to position a handle bore 880 coaxial with the longitudinal axis 802. Next the tube 868 and lower spring guide 870 are inserted from the proximal end into the body 862 and through the handle bore 880. The lower spring guide 870 is secured to the handle for example by press fitting welding, bonding, or other suitable means. Next the spring 872 is inserted from the proximal end into the body 862 to engage the lower spring guide 870. Next the upper spring guide is inserted from the proximal end into the body 862 to engage and preload the spring 872. Finally, the clip 876 is inserted from the proximal end into a groove 882 in the body to retain the clamping and guiding mechanism within the body 862. Thus assembled, the tube 868 extends into the space 824 between the guide 860 and foot 812. Moving the handle 866 proximally retracts the tube 868 away from the foot 812 and compresses the spring 872. Releasing the handle 866 allows the spring to extend the tube 868 toward the foot 812. The distal end of the tube 868 includes a bevel 884 and teeth 886 opposing the proximal facing surface 816 of the foot. The guide 860 includes a fixed handle 890 extending radially outwardly from the body 862 to provide a fixed position on the guide 860 for applying counter pressure as will be described below. The guide 860 further includes a depth control stop 892. In the illustrative example of FIGS. 28-30, the stop 892 is in the form of an integral ring extending radially outwardly from the body 862 near the proximal end.

Figure 31:
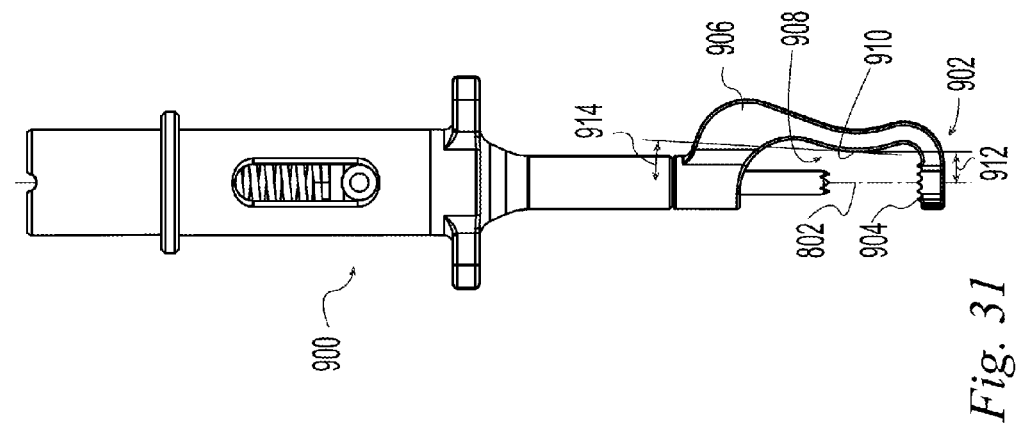
FIG. 31 is a side elevation view of a suture passer similar to that of FIG. 28 but having an alternative distal geometry.

FIG. 31 depicts a suture retriever 900 similar to that of FIGS. 28-30. The suture retriever 900 includes a foot 902 with a proximal facing surface 904 sized and shaped to engage a desired location for a bone tunnel exit and an extension 906 sized and shaped to engage the articular surface of a phalangeal bone. The extension 906 has a curved articular surface engaging portion 908 that is convex toward the longitudinal axis 802. The articular surface engaging portion 908 defines an apex 910 that is radially offset from the longitudinal axis 802 by a radial offset distance 912. The articular surface engaging portion 908 is angled relative to the longitudinal axis such that a tangent line through the apex 910 and coplanar with the longitudinal axis 802 forms an angle 914 with the longitudinal axis. In the illustrative example of FIG. 31, the offset distance 912 is approximately equal to the offset distance of the extension 906 adjacent the proximally facing surface 904 of the foot and is in the range of 1-4 mm. Preferably, the offset distance 912 is approximately 2 mm. As with the retriever of FIGS. 28-30, this offset corresponds to the distance from the edge of the articular surface of the proximal phalanx to the anatomic insertion site of the plantar plate on the plantar aspect of the proximal phalanx of a human foot. Other offset distances may be used for other anatomic sites. The proximal facing surface 904 of the foot, the articular surface engaging portion of the extension, and the longitudinal axis are oriented relative to one another based on human anatomy relating anatomic landmarks to a desired bone tunnel orientation in the bone. For example, with the proximal facing surface of the foot 904 engaging a ligament insertion on the proximal phalanx and the articular surface engaging portion 908 engaging the center of the articular surface of the proximal phalanx at the metatarsophalangeal joint, the longitudinal axis 802 will directed along a desired bone tunnel path. The offset 912 and angle 914 are less than the offset 830 and angle 832 of the retriever of FIG. 30 so that the retrievers 800 and 900 may advantageously be used together as a set to form bone tunnels with proximal entrances offset different distances from the articular surface such that the bone tunnels do not intersect.

Figure 32:
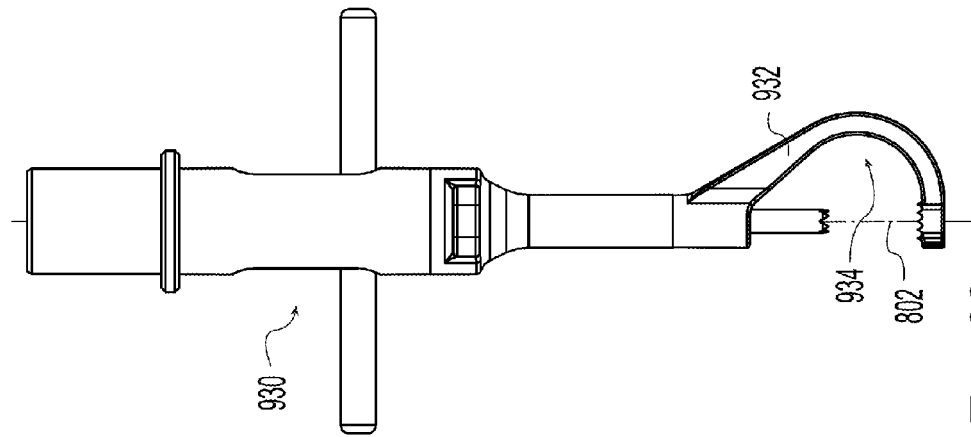
FIG. 32 is a side elevation view of a suture passer similar to that of FIG. 28 but having an alternative distal geometry.

FIG. 32 depicts a suture retriever 930 similar to that of FIGS. 28-30. The extension 932 is bowed outwardly away from the longitudinal axis 802 and presents a concave surface 934 toward the longitudinal axis 802. The retriever 930 is not intended to reference the articular surface but instead the extension is shaped to extend around bone portions of arbitrary shape allowing the retriever 930 to be used at a variety of different locations and a various desired orientations to form a bone tunnel and pass a suture through the tunnel.

FIGS. 33-37 depict a suture shuttle assembly 1000 including a shuttle suture assembly 1002 and a shuttle inserter 1030. The shuttle suture assembly 1002 includes a suture loop 1004 and a stopper 1006. The stopper includes a body having a proximal end 1008 and a distal end 1010. A post 1012 extends from the proximal end distally and includes an eyelet 1014. An intermediate portion 1016 of the body extends from the post 1012 distally. The intermediate portion 1016 is enlarged radially relative to the post 1012 and defines a proximally facing proximal shoulder 1018. A distal portion 1020 is enlarged radially relative to the intermediate portion 1016 and defines a proximally facing distal shoulder 1022. The distal portion 1020 is chamfered to that it narrows distally. The body is separated into opposed cantilevered legs joined at the proximal end and separated by a space 1024 that opens distally. The distal portion 1020 is sized so that the chamfer will start into the opening 814 of the foot 812 of the suture retrievers and the legs will elastically flex inwardly to allow the distal portion to pass through the opening 814. Upon exiting the opening, the legs will flex outwardly due to the resilience of the stopper. When flexed outwardly the distal shoulder 1022 will catch on the distal surface of the foot and prevent the stopper from pulling proximally back through the opening 814. The intermediate portion 1016 is sized to form a friction fit within the opening 814 so it will not fall all the way through. The suture loop 1004 is passed through the eyelet 1014 so that four strands of suture extend away from the stopper. In the illustrative example of FIGS. 33-37, the suture loop 1004 is formed by knotting the ends of a suture and the knotted portion 1026 and a bight 1028 opposite the knotted portion 1026 terminate the four strands.

The shuttle inserter 1030 includes a proximal handle 1032 having an outer surface 1034 and an interior bore 1036 extending through the handle proximally to distally and defining a longitudinal axis 1038. The bore 1036 is enlarged proximally to form an O-ring groove 1040. The bore 1036 is enlarged distally to form an enlarged hollow space 1042. A tube 1044 is inserted into the bore 1036 and secured such as by press fitting, welding, bonding, or other suitable means. The tube 1044 extends distally through the hollow space 1042 and distally away from the handle to a distal end 1046.

The shuttle suture 1002 assembly is loaded into the shuttle inserter 1030 by passing the knotted portion 1026 and bight 1028 through the tube 1044 from the distal end proximally through the handle and out the proximal end 1048 of the inserter. The bight 1028 is draped over the proximal end of the handle 1032. The knotted portion 1026 is passed through an O-ring 1052 and a portion of the suture loop adjacent the knotted portion 1026 and below the O-ring is pulled out radially to form a doubled bight 1050 which is draped over the proximal end of the handle 1032. The O-ring 1052 is pressed into the O-ring groove 1040 and traps the bight 1028 and doubled bight 1050 between the O-ring 1052 and groove 1040. The bight 1028 and doubled bight 1050 may be pulled to remove slack from the suture loop 1004 and seat the stopper 1006 in the distal end of the tube 1044. The post 1012 is sized to fit within the tube 1044 and the proximal shoulder 1018 is sized to abut the distal end 1046.

Figure 38:
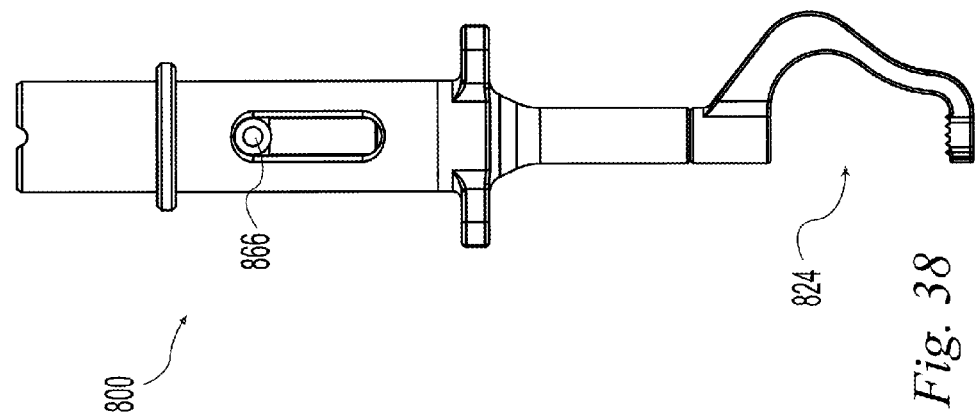

FIGS. 38-50 illustrate the suture passers of FIGS. 28 and 30 and the suture shuttle assembly of FIG. 33 in use to pass sutures through a proximal phalanx of a human foot adjacent to the metatarsophalangeal joint. In FIG. 38, the handle 866 has been moved proximally to retract the tube 868 from the bone receiving space 824.

Figure 39:
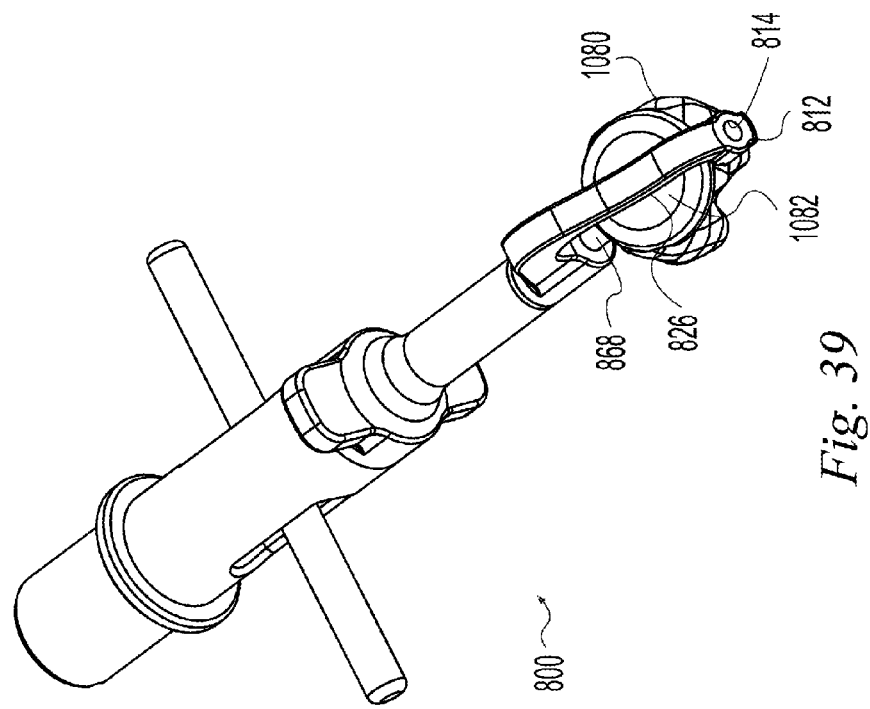

FIGS. 39-41 depict front, side, and top views of a single placement of the suture retriever 800 on the proximal phalanx 1080 with the opening 814 in the foot 812 positioned at a desire exit for a bone tunnel. For example, it has been positioned at the location of an anatomic soft tissue insertion. In the illustrative technique of FIGS. 39-41, the foot 812 is positioned lateral plantar. The articular surface engaging portion 826 is engaged with the center of the articular surface 1082 and the tube 868 has been allowed to move against the bone 1080 under spring pressure to clamp the suture retriever 800 to the bone 1080. The orientation and spacing of the foot 812 and articular surface engaging portion 826, once registered with the anatomic landmarks of the soft tissue insertion and articular surface, establish the location of the tube 868 on the bone 1080 and the tunnel trajectory through the bone. Since a lateral plantar insertion point was referenced, the tube is positioned by the retriever geometry at a medial dorsal location on the bone.

Figure 42:
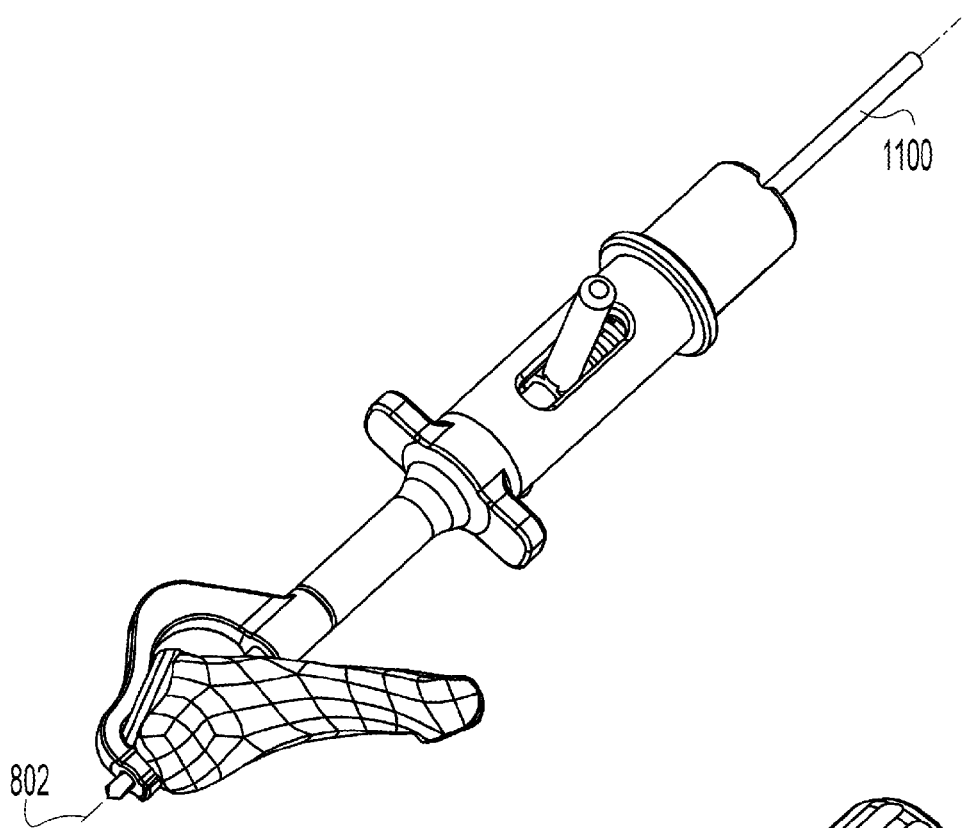

In FIG. 42, a cutter, for example a K-wire 1100, has been guided through the tube 868 to form a bone tunnel through the proximal phalanx 1080 coaxial with the longitudinal axis 802.

Figure 43:
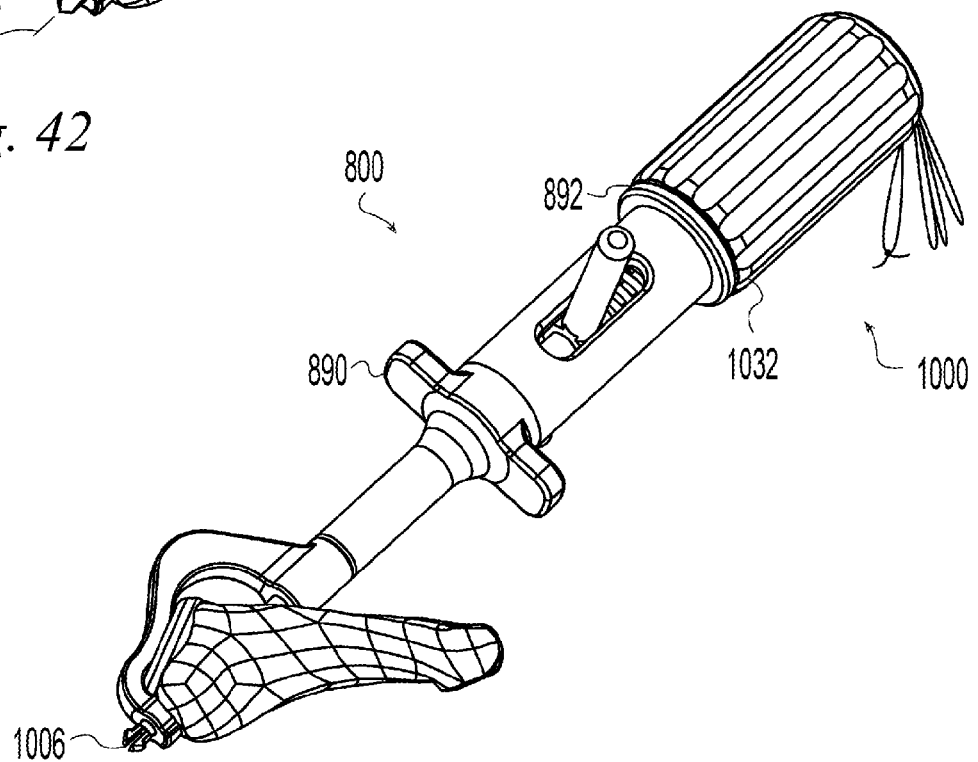

In FIG. 43, the suture shuttle assembly 1000 has been inserted through the tube 868 to guide the stopper 1006 through the bone tunnel and through the opening 814 in the foot of the suture retriever 800. The fixed handle 890 may be used to provide pressure counter to the insertion force. The suture shuttle assembly 1000 is advanced such that the proximal end of the retriever body 862 is received in the hollow 1042 in the distal end of the handle 1032 and until the distal end of the handle 1032 abuts the depth stop 892. The depth stop 892 is positioned, and the shuttle suture assembly sized, to allow the distal portion of the stopper 1006 to pass completely through the opening in the foot so that the distal shoulder 1022 snaps through but to prevent over insertion of the stopper 1006.

Figure 44:
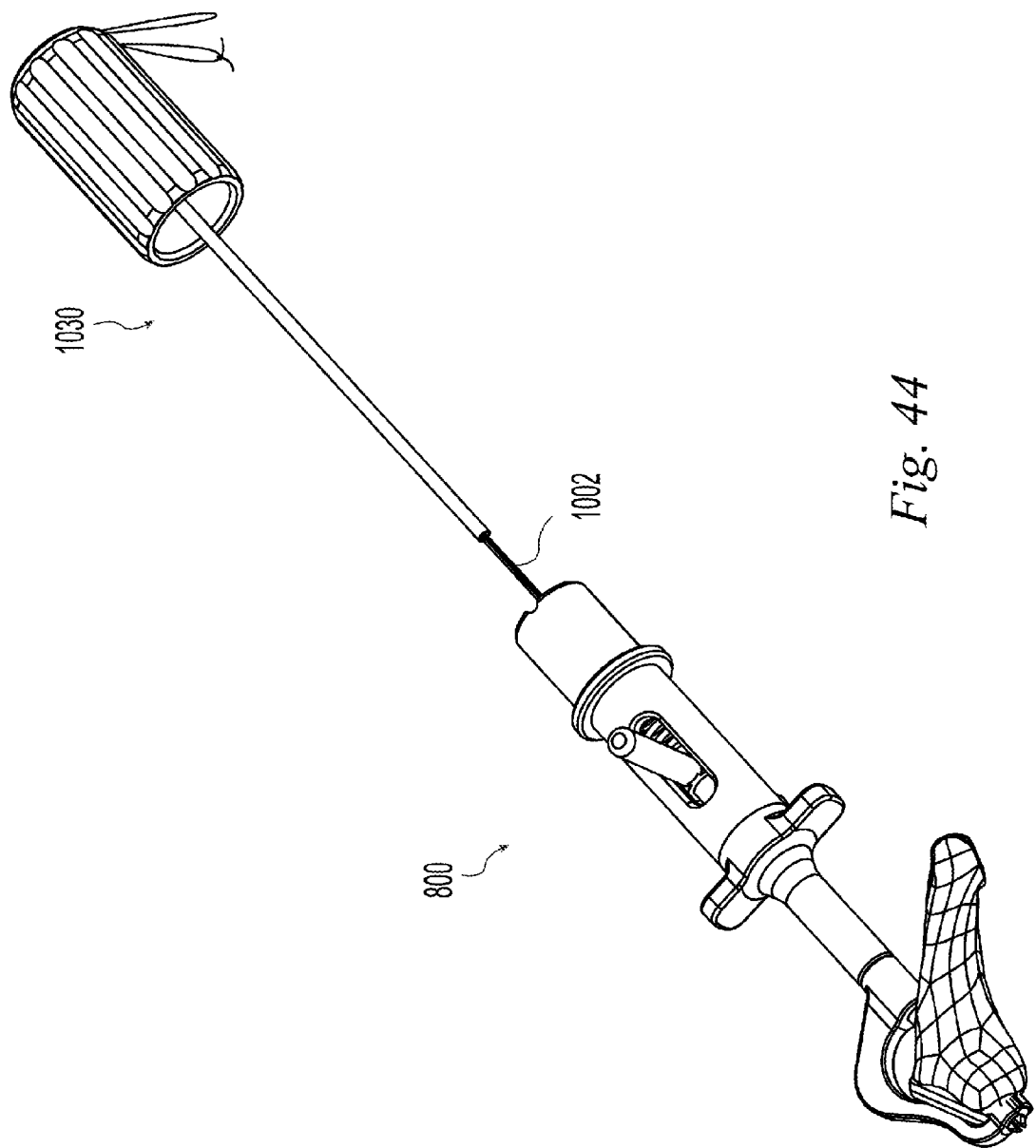

In FIG. 44, the shuttle inserter 1030 has been withdrawn leaving the shuttle suture assembly 1002 extending through the bone tunnel and retriever 800. The distal shoulder 1022 prevents the stopper 1006 from being pulled proximally back through the opening 814 in the foot.

Figure 45:
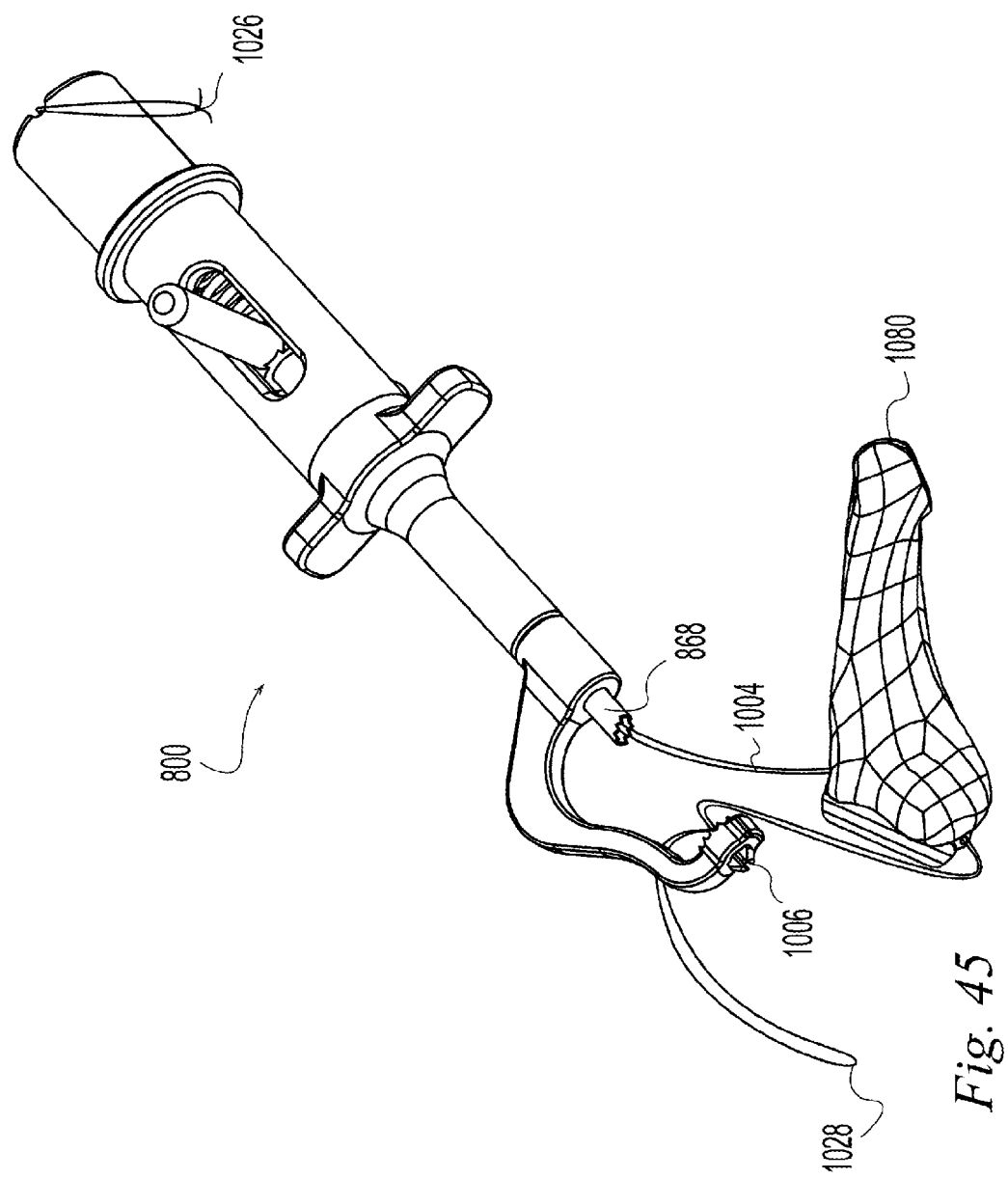

In FIG. 45, the suture retriever 800 has been moved away from the proximal phalanx. In the illustrative example of FIG. 45, the knotted end 1026 is held by the user while the retriever 800 is moved and the bight 1028 is allowed to pull through the tube 868. At this point, both ends of the suture loop 1004 are outside of the surgical site. Further movement of the retriever 800 away from the bone pulls the bight 1028 through the eyelet in the stopper 1006. Releasing the knotted portion 1026 and further moving the retriever 800 allows the knotted end 1026 to pull through the tube 868. The bight 1028 and knotted portion 1026 may then be retrieved by the user and positioned as desired. For example, the bight 1028 and knotted portion 1026 may be retained in a surgical clamp outside of the surgical site to aid in suture management.

In FIG. 46, the bight 1028 is shown trailing below the proximal phalanx for clarity of illustration. However, the bight 1028 would preferably be pulled dorsally to a position adjacent the knotted portion 1026 through the dorsal incision as shown in FIG. 49.

Figure 48:
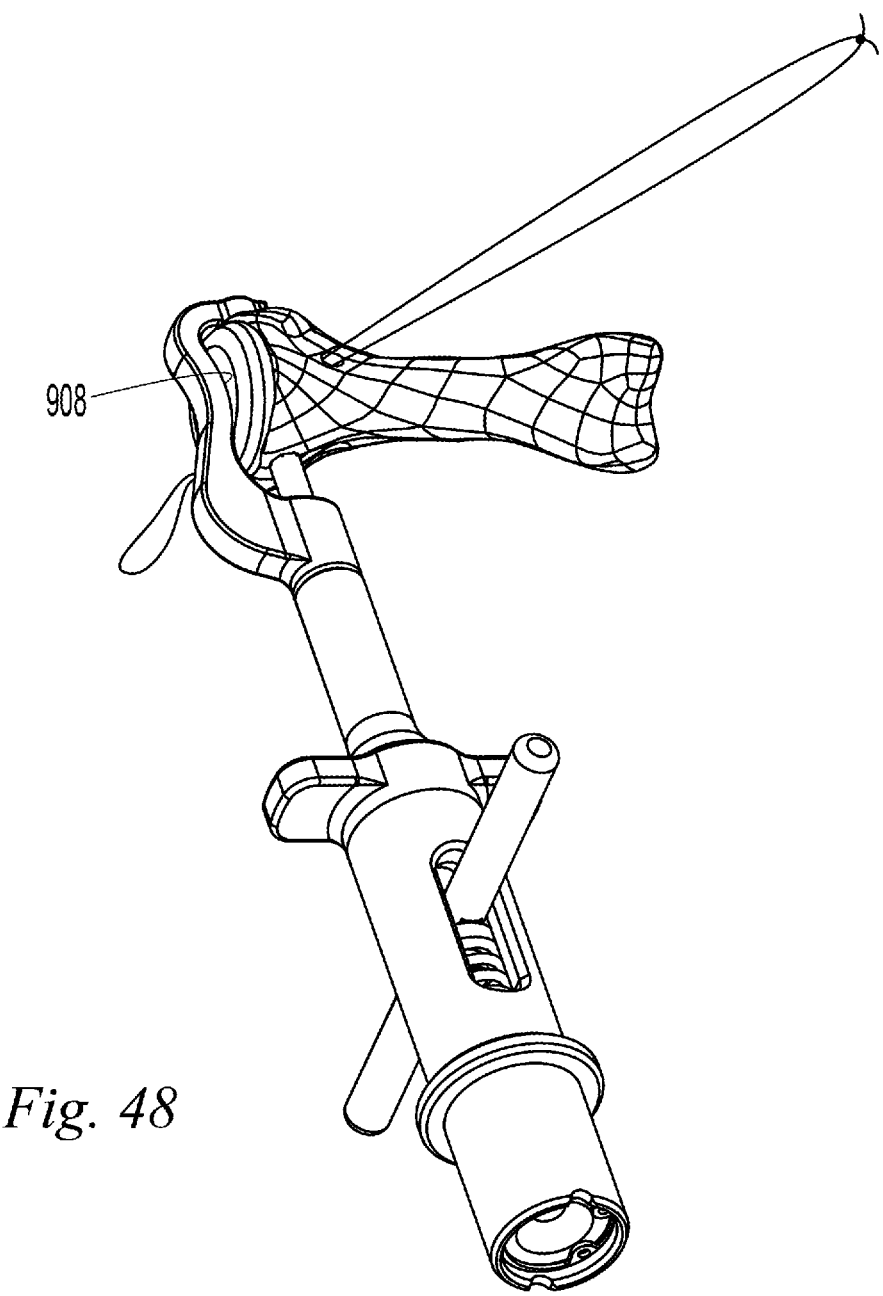

In FIGS. 46-48, the suture retriever 900 has been placed on the proximal phalanx 1080 with the foot 902 positioned at a desire exit for a bone tunnel. In the illustrative technique of FIGS. 46-48, the foot 902 is positioned medial plantar. The articular surface engaging portion 908 is engaged with the center of the articular surface 1082 and the tube 868 has been allowed to move against the bone 1080 under spring pressure to clamp the suture retriever 900 to the bone 1080. The orientation and spacing of the foot 902 and articular surface engaging portion 908, once registered with the anatomic landmarks of the soft tissue insertion and articular surface, establish the location of the tube 868 on the bone 1080 and the tunnel trajectory through the bone. Since a medial plantar insertion point was referenced, the tube is positioned by the retriever geometry at a lateral dorsal location on the bone. Since the radial offset of the retriever 900 is less than the offset of the retriever 800, the bone tunnel will be positioned proximal to the bone tunnel produced with the longer offset retriever 800 and the tunnels will not intersect. The second bone tunnel is drilled and the shuttle suture placed as described relative to the first bone tunnel.

Figure 49:
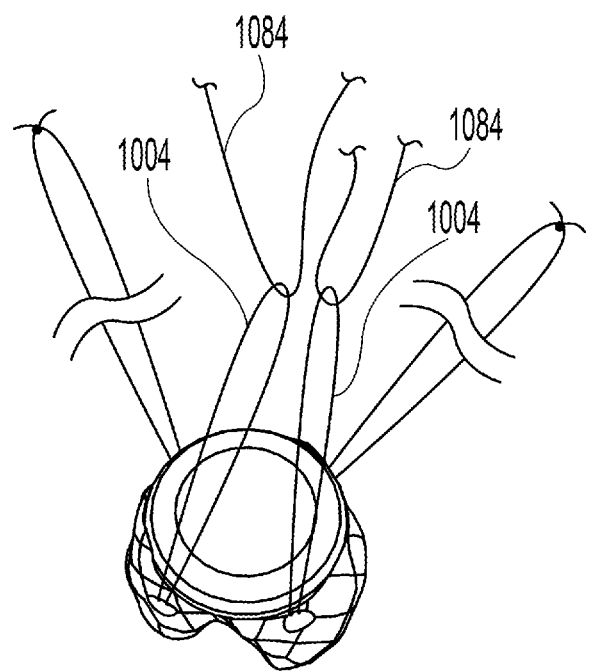

In FIG. 49, shuttle suture loops 1004 are shown extending from each of the bone tunnels and definitive repair sutures 1084 are shown inserted through each of the loops 1004.

Figure 50:
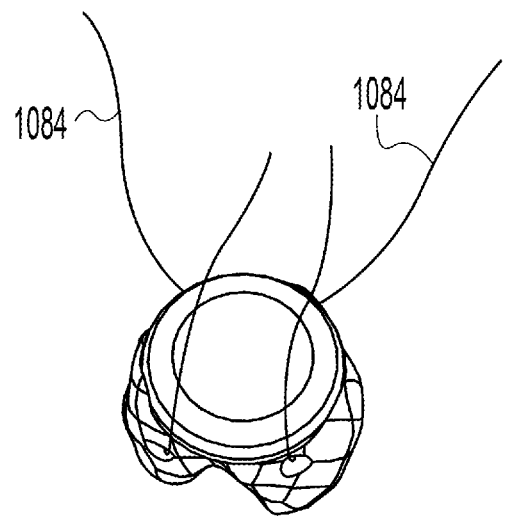

In FIG. 50, the shuttle sutures 1004 have been pulled to pass the definitive sutures 1084 through the bone tunnels.

The illustrative examples have shown instruments and methods in use to pass a suture through a bone tunnel. However, a suture passed by the suture passer may be used in any way that sutures are known to be used. Single strands, double strands, or any number of strands may be passed. Likewise one or more loops may be passed. Any of these may be used as a definitive suture in a repair or reconstruction, as a shuttle for pulling another material into a desired position, or for any other purpose. The present invention is not limited to the specific instruments and methods depicted.

What is claimed is:

1. A suture passer system for passing a suture through a bone, the suture passer system comprising:
   a first suture retriever having a receiver and a guide aligned with the receiver along a guide axis, the receiver having an opening coaxial with the guide axis, the receiver and guide being spaced apart and defining a bone receiving space therebetween;
   a suture assembly, the suture assembly comprising a suture and a plug connected to the suture, the guide being operable to guide the suture along the guide axis and the opening in the receiver being operable to receive the plug in axial translating relationship between a first proximal position spaced from the opening and a second distal position in which the plug is constrained from movement toward the first position, wherein the plug includes a first radially extending portion operable to engage the receiver and constrain proximal movement; and further comprising a suture inserter, the suture inserter including an elongated tube having a proximal end and a distal end, the tube having an outer surface, the guide being operable to receive the outer surface of the tube in axial sliding relationship, and the plug further comprises a body sized to fit within the tube and a second radially extending portion formed proximal of the first radially extending portion, the second radially extending portion being operable to engage the distal end of the tube to limit proximal translation of the plug into the tube.

2. The suture passer system of claim 1 wherein the inserter includes a suture retainer operable to maintain tension on the suture when the second radially extending portion of the plug is engaged with the distal end of the tube.

3. The suture passer system of claim 1 wherein the first suture retriever and suture inserter comprise a depth stop mechanism operable to limit the distal translation of the inserter relative to the guide to a depth in which the first radially extending portion extends through the opening in the receiver.

4. A suture passer system for passing a suture through a bone, the suture passer system comprising:
a first suture retriever having a receiver and a guide aligned with the receiver along a guide axis, the receiver having an opening coaxial with the guide axis, the receiver and guide being spaced apart and defining a bone receiving space therebetween;
a suture assembly, the suture assembly comprising a suture and a plug connected to the suture, the guide being operable to guide the suture along the guide axis and the opening in the receiver being operable to receive the plug in axial translating relationship between a first proximal position spaced from the opening and a second distal position in which the plug is constrained from movement toward the first position; and
further comprising a cutter engageable with the guide, the guide being operable to guide the cutter along the guide axis to form a tunnel in a bone positioned in the space between the guide and receiver.

5. A suture passer system for passing a suture through a bone, the suture passer system comprising:
a first suture retriever having a receiver and a guide aligned with the receiver along a guide axis, the receiver having an opening coaxial with the guide axis, the receiver and guide being spaced apart and defining a bone receiving space therebetween;
a suture assembly, the suture assembly comprising a suture and a plug connected to the suture, the guide being operable to guide the suture along the guide axis and the opening in the receiver being operable to receive the plug in axial translating relationship between a first proximal position spaced from the opening and a second distal position in which the plug is constrained from movement toward the first position, wherein the first suture retriever further comprises a clamping mechanism operable to clamp a bone between the guide and receiver, and wherein the clamping mechanism is resiliently biased distally.

6. The suture passer system of claim 5 wherein the clamping mechanism comprises a clamp handle being operable to overcome the distal bias and move the clamping mechanism from a closed position toward an open position.

7. The suture passer system of claim 6 wherein the first suture retriever has a proximal end and the clamp handle is moveable axially relative to the proximal end of the first suture retriever, the first suture retriever further comprising a fixed handle, the fixed handle being spaced a fixed distance from the proximal end of the first suture retriever.

8. A suture passer system for passing a suture through a bone, the suture passer system comprising:
a first suture retriever having a receiver and a guide aligned with the receiver along a guide axis, the receiver having an opening coaxial with the guide axis, the receiver and guide being spaced apart and defining a bone receiving space therebetween;
a suture assembly, the suture assembly comprising a suture and a plug connected to the suture, the guide being operable to guide the suture along the guide axis and the opening in the receiver being operable to receive the plug in axial translating relationship between a first proximal position spaced from the opening and a second distal position in which the plug is constrained from movement toward the first position, wherein the receiver includes a first reference portion and the first suture retriever further comprises a second reference portion between the receiver and guide, the guide axis being oriented relative to the first and second reference portions based on human anatomy relating anatomic landmarks to a desired bone tunnel orientation in the bone.

9. The suture passer system of claim 8 wherein the second reference portion is a surface offset radially from the guide axis by a radial offset distance.

10. The suture passer system of claim 9 wherein the second reference portion is convex toward the guide axis.

11. The suture passer system of claim 9 wherein the first reference portion is a proximally facing surface adjacent the opening in the receiver.

12. The suture passer system of claim 9 further comprising a second suture retriever having a receiver with a first reference portion and a guide aligned with the receiver along a guide axis, the receiver having an opening coaxial with the guide axis, the receiver and guide being spaced apart and defining a bone receiving space therebetween, the suture retriever further comprising a second reference portion between the receiver and guide, the guide being oriented relative to the first and second reference portions based on human anatomy relating anatomic landmarks to a desired bone tunnel orientation in the bone, the second reference portion being a surface offset radially from the guide axis by a radial offset distance, the radial offset distance of the first suture retriever being greater than the radial offset distance of the second suture retriever.

13. A method comprising:
positioning a receiver of a first suture retriever at a first position on a bone adjacent a bone joint;
guiding a cutter with the suture retriever along a guide axis to form a tunnel through the bone aligned with the receiver;
guiding a suture with the suture retriever along the guide axis to pass a first portion of the suture through the bone tunnel until the first portion of the suture is received by the receiver;
retaining the first portion with the receiver; and
moving the receiver away from the first position to advance the suture relative to the bone tunnel.

14. The method of claim 13 wherein the first portion of the suture includes a plug and the plug is received by the receiver.

15. The method of claim 14 wherein the plug includes an elastic material having a radially projecting portion.

16. The method of claim 15 wherein the plug includes a nitinol wire.

17. The method of claim 14 wherein the receiver includes an opening and the method further comprises passing the plug from a proximal position distally into the opening causing it to compress as it passes into the opening and then expand to restrain the plug against proximal motion relative to the opening.

18. The method of claim 13 wherein the suture is a shuttle suture, the method further comprising: shuttling a second suture through the bone tunnel with the shuttle suture.

19. The method of claim 13 wherein the receiver includes a first reference portion and positioning the receiver comprises positioning the first reference portion at the first position, the method further comprising: positioning a second reference portion in contact with an articular surface of the bone, the guide axis being fixed relative to the first and second reference portions.

20. The method of claim 19 wherein the second reference portion of the first suture retriever is offset radially from the guide axis by a radial offset distance.

21. The method of claim 19 further comprising:
positioning a receiver of a second suture retriever at a first position on a bone adjacent a bone joint;

positioning a second reference portion of the second suture retriever in contact with an articular surface of the bone, the second suture retriever having a guide axis being fixed relative to the first and second reference portions, the second reference portion of each suture retriever being offset radially from the guide axis by a radial offset distance, the radial offset distance of one of the first and second suture retrievers being greater than the radial offset distance of the other suture retriever;

guiding a cutter with the second suture retriever along the guide axis to form a second tunnel through the bone aligned with the receiver;

guiding a second suture with the second suture retriever along the guide axis to pass a first portion of the second suture through the second bone tunnel until the first portion of the second suture is received by the receiver;

retaining the first portion with the receiver; and moving the receiver away from the first position to advance the suture relative to the bone tunnel.

* * * * *